US012135291B2

(12) United States Patent
Kozicki et al.

(10) Patent No.: US 12,135,291 B2
(45) Date of Patent: *Nov. 5, 2024

(54) SYSTEM FOR ANALOG LIGHT MEASURING AND PHOTON COUNTING IN CHEMILUMINESCENCE MEASUREMENTS

(71) Applicant: Beckman Coulter, Inc., Brea, CA (US)

(72) Inventors: Brian Kozicki, Saint Louis Park, MN (US); Creigh Thompson, Chaska, MN (US); Richard Wolf, Savage, MN (US); Laura Holmes, Minnetonka, MN (US); David Sorrentino, Chaska, MN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/225,594

(22) Filed: Jul. 24, 2023

(65) Prior Publication Data
US 2024/0027352 A1 Jan. 25, 2024

Related U.S. Application Data

(63) Continuation of application No. 16/648,609, filed as application No. PCT/US2018/051682 on Sep. 19, 2018, now Pat. No. 11,754,504.
(Continued)

(51) Int. Cl.
*G01N 21/27* (2006.01)
*G01J 1/44* (2006.01)
*G01N 21/76* (2006.01)

(52) U.S. Cl.
CPC ............ *G01N 21/76* (2013.01); *G01J 1/44* (2013.01); *G01N 21/27* (2013.01); *G01N 21/272* (2013.01);
(Continued)

(58) Field of Classification Search
CPC ...... G01N 21/272; G01N 21/27; G01N 21/76; G01N 33/5302; G01N 2201/127;
(Continued)

(56) References Cited

U.S. PATENT DOCUMENTS 3,918,817 A * 11/1975 Posgate ................. G01N 21/51
356/442
4,363,551 A * 12/1982 Achter ................... G01N 21/51
356/338
(Continued)

FOREIGN PATENT DOCUMENTS

JP 4902582 B2 1/2012

OTHER PUBLICATIONS

"Machine translation of the claims and the description of document 230364EP-EINV—D05—MT JP2013072727A, (Apr. 22, 2013)", 12 pgs.
(Continued)

*Primary Examiner* — Sang H Nguyen
(74) *Attorney, Agent, or Firm* — Schwegman Lundberg & Woessner, P.A.

(57) ABSTRACT

Assays (100) may be performed with a luminometer (400) having a chassis (405) that may include a reaction vessel chamber (610). The luminometer (400) may also include a light passage (640) that intersects the reaction vessel chamber (610). The luminometer (400) may also include a cap (415) that, when in a closed configuration, prevents light emitted by external sources from entering the reaction vessel chamber (610) and from entering the light passage (640). The cap (415) may provide access to the reaction vessel chamber (610) when in an open configuration. The luminometer (400) may also include a calibration light source (460) optically coupled to one end of the light passage (640) and a light detector (630) optically coupled to another end of
(Continued)

the light passage (640). The light detector (630) may include a sensing element for receiving light from the light passage (640).

20 Claims, 23 Drawing Sheets

Related U.S. Application Data

(60) Provisional application No. 62/560,636, filed on Sep. 19, 2017, provisional application No. 62/560,638, filed on Sep. 19, 2017.

(52) U.S. Cl.
CPC .. *G01J 2001/444* (2013.01); *G01N 2201/022* (2013.01); *G01N 2201/12753* (2013.01)

(58) Field of Classification Search
CPC ..... G01N 2201/1241; G01N 2201/022; G01N 2201/12753; G01N 2021/135; G01J 1/44; G01J 2001/444
See application file for complete search history.

(56) References Cited

U.S. PATENT DOCUMENTS

| | | | | |
|---|---|---|---|---|
| 5,963,318 | A * | 10/1999 | Held | G01N 21/0303 356/244 |
| 6,486,947 | B2 * | 11/2002 | Modlin | B01L 3/50853 356/244 |
| 6,924,498 | B2 | 8/2005 | Feldsine et al. | |
| 8,638,433 | B1 * | 1/2014 | Amend | G01J 3/0248 356/319 |
| 9,618,455 | B2 * | 4/2017 | Cohen | G01N 21/253 |
| 11,879,851 | B2 | 1/2024 | Wolf et al. | |
| 2008/0031094 | A1 * | 2/2008 | Laugharn, Jr. | G01N 1/28 367/138 |
| 2014/0113277 | A1 * | 4/2014 | Thomas | G01N 35/026 435/5 |
| 2014/0206412 | A1 * | 7/2014 | DeJohn | C12Q 1/686 455/556.1 |
| 2023/0194433 | A1 | 6/2023 | Wolf et al. | |

OTHER PUBLICATIONS

"Machine translation of the description and the claims of document 230364EP-EINV—D08—MT WO2006066460A1, (Jun. 29, 2006)", 7 pgs.

"Machine translation of the description and the claims of document 230364EP-EINV—010—MT JP2000046734A, (Feb. 18, 2000)", 26 pgs.

"Machine translation of the claims and the description of 230364EP-EINV—003—MT JP4902582B2, (Jan. 13, 2012)", 13 pgs.

"U.S. Appl. No. 18/109,980, Corrected Notice of Allowability mailed Dec. 8, 2023", 2 pgs.

"U.S. Appl. No. 18/109,980, Notice of Allowance mailed Jun. 14, 2023", 9 pgs.

"U.S. Appl. No. 18/109,980, Notice of Allowance mailed Oct. 16, 2023", 6 pgs.

"U.S. Appl. No. 18/109,980, PTO Response to Rule 312 Communication mailed Sep. 1, 2023", 2 pgs.

"U.S. Appl. No. 18/542,333, Preliminary Amendment filed May 2, 2024", 6 pgs.

"Notice of Opposition to a European Patent Application No. EP18783245.6 mailed on Jul. 9, 2022", 41 pgs.

Hamamatsu, Photonics K K, "Photomultiplier Tubes—Basics and Applications", Iwata City, JP: 230364EP-EINV, (2007), 323 pgs.

Hamamatsu, Photonics K K, "Photon Counting Using Photomultiplier Tubes", Iwata City, JP, (2005), 28 pgs.

U.S. Appl. No. 16/648,609 U.S. Pat. No. 11,754,504, filed Mar. 18, 2020, System for Analog Light Measuring and Photon Counting in Chemiluminescence Measurements.

U.S. Appl. No. 16/648,622 U.S. Pat. No. 11,604,146, filed Mar. 18, 2020, Analog Light Measuring and Photon Counting With a Luminometer System for Assay Reactions in Chemiluminescence Measurements.

U.S. Appl. No. 18/109,980 U.S. Pat. No. 11,879,851, filed Feb. 15, 2023, Analog Light Measuring and Photon Counting in Chemiluminescence Measurements.

U.S. Appl. No. 18/542,333, filed Dec. 15, 2023, Analog Light Measuring and Photon Counting in Chemiluminescence Measurements.

* cited by examiner

SYSTEM FOR ANALOG LIGHT MEASURING AND PHOTON COUNTING IN CHEMILUMINESCENCE MEASUREMENTS

CROSS REFERENCE TO RELATED APPLICATIONS

This application is a continuation of U.S. application Ser. No. 16/648,609, filed Mar. 18, 2020, which application is a U.S. National Stage Filing under 35 U.S.C. 371 from International Application No. PCT/US2018/051682, filed on Sep. 19, 2018, and published as WO 2019/060375 on Mar. 28, 2019, which application claims the benefit of and priority to U.S. Provisional Patent Application No. 62/560,636, filed Sep. 19, 2017, entitled SYSTEM FOR ANALOG LIGHT MEASURING AND PHOTON COUNTING IN CHEMILUMINESCENCE MEASUREMENTS, and to U.S. Provisional Patent Application No. 62/560,638, filed Sep. 19, 2017, entitled ANALOG LIGHT MEASURING AND PHOTON COUNTING IN CHEMILUMINES-CENCE MEASUREMENTS, the disclosures of which are incorporated herein in their entireties for all purposes. This application is related to U.S. Patent Application, which is a U.S. National Stage Filing under 35 U.S.C. 371 from International Application No. PCT/US2018/051679, filed Sep. 19, 2018, and published as WO 2019/060373 on Mar. 28, 2019, the disclosures of which are incorporated herein in their entireties for all purposes.

BACKGROUND

Many medical conditions can be diagnosed by sophisticated testing (i e, an assay) that includes combining sample fluids from a patient with reagents containing antibodies or antigens that are tailored to bond only with an analyte in the sample fluid that the assay is meant to measure. The fluids and reagents are typically combined in a reaction vessel (e.g., a cuvette). At least one reagent can include a light emitting enzyme (e.g., alkaline phosphatase) that directly or indirectly bonds with the analyte such that a greater amount of light emitted during the testing indicates a greater amount of the analyte in the sample. During the testing process, a light detecting device, typically a photomultiplier tube ("PMT"), is used to measure the amount of light emitted (e.g., by counting apparent photons) by the light emitting enzymes. Electrical hardware connected to the PMT may provide an output value related to the optical power of the emitted light by counting individual photons that strike a photocathode of the PMT. The output value may be transformed to a relative light unit ("RLU") value. However, as a rate of the photons striking the photocathode increases, the probability of two or more photons striking the photocathode simultaneously or nearly simultaneously increases. If two or more photons strike the photocathode within a sufficiently small period of time, these photons may only be counted as a single photon (i.e., an apparent single photon strike). The limit of the ability of a system to distinguish a pair of photons that strike nearly simultaneously is known as pulse pair resolution. The previous electrical hardware cannot distinguish a true single photon from a plurality of photons striking together or nearly together when a time between strikes is below its pulse pair resolution and thus miscounts the photons and underreports the optical power received by the PMT. Previous systems have suffered from various issues, including the undercounting of photons emitted at high rates, that make their test results unreliable and/or insensitive. For example, as the optical power increases, the PMT becomes unable to accurately measure the incoming light. The relationship between optical power of the light source and the electrical signal generated by the electrical hardware connected to the PMT (which is used to calculate the RLU value of the light source) is or becomes non-linear. Additionally, non-linear output requires cumbersome analysis to provide an RLU value. Further, existing systems suffer from external light source photon contamination, reaction vessel position inaccuracies, photon contamination from adjacent reaction vessels, temperature variability, and so forth, all of which threaten to compromise the accuracy of the test results. Accordingly, new and improved systems and methods are needed.

BRIEF SUMMARY

Described herein are systems and methods for performing an assay using a system that mitigates temperature disturbances, photon contamination from external light sources, photon contamination from other reaction vessels, and reaction vessel position inaccuracies. Further, the systems and methods described herein provide a substantial extension in the signal linearity of the system output response over prior systems. Extended signal linearity improves the accuracy of test results that have high output response values (relative light unit ("RLU") values). Additionally, the systems and methods described herein provide signal linearity at low ranges through the crossover point to high ranges, such that there is no offset, which mitigates the need for manual analysis of the system results.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system for performing an assay, the system including a chassis that can include a reaction vessel chamber. The chassis may also include a light passage intersecting the reaction vessel chamber. The light passage may have two ends. The system may also include a cap that, when in a closed configuration, forms a dark chamber by preventing light emitted by external sources from entering the reaction vessel chamber. The cap, when in an open configuration, provides access to the reaction vessel chamber. The system may include a calibration light source optically coupled to one end of the light passage. The system may include a sensing element for receiving light from the light passage. Other embodiments of this aspect include corresponding computer systems, apparatus, and computer programs recorded on one or more computer storage devices, each configured to perform the actions of the methods.

Implementations may include one or more of the following features. Optionally the chassis further includes a first portion of a labyrinth seal at an opening to the reaction vessel chamber. Optionally, the cap includes a second portion of the labyrinth seal. The second portion of the labyrinth seal of the cap can engage with the first portion of the labyrinth seal when the cap is in the closed configuration. Optionally, the dark chamber is formed when the second portion of the labyrinth seal engages with the first portion of the labyrinth seal. Optionally, the dark chamber is formed when an opening angle between the cap and the chassis is seven degrees or less from the closed configuration. Optionally, the second portion of the labyrinth seal of the cap and the first portion of the labyrinth seal are non-contacting.

Optionally, the first portion of the labyrinth seal includes a first wall positioned about the opening to the reaction vessel chamber, the first wall defining a first external diameter and a first height. The first portion of the labyrinth seal can also include a first circular trough having a first trough diameter larger than the first external diameter, the first circular trough being concentrically positioned about the opening to the reaction vessel chamber. The first portion of the labyrinth seal can also include a second wall positioned about the first circular trough, the second wall defining a second external diameter and a second height that is less than the first height. The first portion of the labyrinth seal can also include a second circular trough having a second trough diameter larger than the first trough diameter, the second circular trough being concentrically positioned around the opening to the reaction vessel chamber. Optionally, the second portion of the labyrinth seal can include a third wall defining a third external diameter larger than the first external diameter. The second portion of the labyrinth seal can include a third circular trough having a third trough diameter larger than the third external diameter, the third circular trough being concentrically positioned about the third wall. The second portion of the labyrinth seal can include a fourth wall positioned about the third circular trough, the fourth wall defining a fourth external diameter larger than the third trough diameter and larger than the second external diameter. Optionally, when the cap is in the closed configuration, the second portion of the labyrinth seal of the cap engages with the first portion of the labyrinth seal such that the fourth wall is positioned within the second circular trough, the third wall is positioned within the first circular trough and between the first wall and the second wall, and the second wall is positioned within the third circular trough and between the third wall and the fourth wall.

Optionally, the system can include a cap arm coupled to the cap. The system may also include a motor coupled to the cap arm, where operation of the motor changes a configuration of the cap between the closed configuration and the open configuration. Optionally, the system can further include a cap sensor that senses the configuration of the cap. The system may also include a shutter communicatively coupled to the cap sensor and adapted to block light present in the light passage from entering the sensing element when the shutter is closed, where the shutter closes when the cap sensor indicates the cap is in the open configuration. The shutter can be an electronic shutter.

Optionally, the system can include a light detector bracket that couples the light detector to the chassis, where the light detector bracket forms a portion of the reaction vessel chamber.

Optionally, the system can include a heating element attached to an external portion of the chassis. The system may also include a thermistor positioned within a thermistor passage of the chassis and electrically coupled to a control system. The system may also include a thermal barrier positioned below the chassis. Optionally, the chassis is aluminum. Optionally, the heating element is activated by the control system based on a temperature of the chassis as measured by the thermistor to maintain a predetermined temperature of the chassis. An example predetermined temperature of the chassis may be 37 degrees Celsius. Optionally, the system can include a thermal cavity within the chassis, and the light detector may be at least partially positioned within the thermal cavity. The system may also include a thermal cover positioned over an opening of the thermal cavity. The system may also include a thermally conductive gasket that thermally couples the thermal cover to the chassis. The conductive gasket can be, for example, conductive silicone (e.g. conductive silicone 65 durometer with conductive pressure sensitive adhesive) Optionally, the thermal cavity and the thermal cover substantially define an enclosed volume. Optionally, the light detector is positioned within the enclosed volume.

Optionally, the reaction vessel chamber includes a first portion of a kinematic spherical joint adjacent to a bottom of the reaction vessel chamber. The first portion of a kinematic cylindrical joint can be adjacent to atop of the reaction vessel chamber. Optionally, the reaction vessel can include a fin that, when the reaction vessel is placed in the reaction vessel chamber, forms a second portion of the kinematic cylindrical joint. Optionally, the reaction vessel can include a nose such that, when the reaction vessel is placed in the reaction vessel chamber, forms a second portion of the kinematic spherical joint. Optionally, the reaction vessel is positioned within the reaction vessel chamber by the kinematic cylindrical joint and the kinematic spherical joint. Optionally, an opening to the reaction vessel chamber includes a tapered portion adapted to guide the reaction vessel into the reaction vessel chamber. Optionally, the tapered portion is adjacent the first portion of the kinematic cylindrical joint. Optionally, the fin is spaced less than a fin thickness from the tapered portion when the reaction vessel is held within the reaction vessel chamber by the kinematic cylindrical joint and the kinematic spherical joint. Optionally, the tapered portion is adapted to provide relief clearance for the fin upon removal of the reaction vessel from the reaction vessel chamber.

Optionally, the calibration light source includes an aluminum housing having an aperture positioned at the first end of the light passage. The system may also include a light emitting diode ("LED"). The system may also include a photodiode. The system may also include a filter positioned between the first end of the light passage and the aperture. Optionally, the light detector includes a PMT configured to measure a relative light unit ("RLU") measurement of light within the light passage.

Optionally, the system may further include a reaction vessel positioned within the reaction vessel chamber. The reaction vessel may contain a sample having a meniscus at the top. Optionally, the light detector may include an aperture for receiving light from the light passage and a light detector bracket that includes the aperture. Optionally, the light detector bracket is positioned to shield the meniscus from a view of the aperture.

Optionally, the chassis includes a housing, the housing enclosing the reaction vessel chamber, the light passage, the thermistor passage, and the thermistor. Implementations of the described techniques may include hardware, a method or process, or computer software on a computer-accessible medium.

Another general aspect includes a light measurement system for performing an assay. The light measurement system may include a housing that includes a reaction vessel chamber for holding a reaction vessel. The reaction vessel chamber may include a first reaction vessel locating feature adapted to interface with a first feature of the reaction vessel to transitionally couple the reaction vessel chamber to the reaction vessel at a first point in three mutually orthogonal directions. The reaction vessel chamber may also include a second reaction vessel locating feature adapted to interface with a second feature of the reaction vessel to translationally couple the reaction vessel chamber to the reaction vessel at a second point, spaced from the first point, in two mutually orthogonal directions, the two mutually orthogonal directions each orthogonal to a chamber axis defined by the reaction vessel chamber and located on the first point and the second point.

Another general aspect includes a system for performing an assay. The system may include a chassis that includes a reaction vessel chamber. The chassis may also include a light passage having a first end and a second end. The light passage may intersect the reaction vessel chamber. The chassis may also include a first portion of a labyrinth seal. The system may also include a cap that has a second portion of the labyrinth seal. Optionally, when the cap is in a closed configuration, the second portion of the labyrinth seal engages with the first portion of the labyrinth seal to form a dark chamber by preventing light emitted by external light sources from entering the reaction vessel chamber. The system may also include a light detector optically coupled to the first end of the light passage. Optionally, the light detector includes a sensing element for receiving light from the light passage.

Optionally, the first portion of the labyrinth seal includes a first set of intermeshing walls. Optionally, the second portion of the labyrinth seal includes a second set of intermeshing walls. Optionally, when the cap is in the closed configuration, one of the first set of intermeshing walls is positioned between two of the second set of intermeshing walls. Optionally, the first portion of the labyrinth seal does not contact the second portion of the labyrinth seal when the cap is in the closed configuration.

BRIEF DESCRIPTION OF THE DRAWINGS

A further understanding of the nature and advantages of various examples may be realized by reference to the following figures.

DETAILED DESCRIPTION

Embodiments described herein include systems and methods including systems using a photomultiplier tube ("PMT") for performing an assay and systems and methods with extended output signal linearity. The system includes components used to mitigate temperature disturbances, photon contamination from external light sources, photon contamination from other reaction vessels, and reaction vessel position inaccuracies that impact assay output measurements.

In the following description, for the purposes of explanation, specific details are set forth in order to provide a thorough understanding of embodiments of the present disclosure. However, it will be apparent that various embodiments may be practiced without these specific details. The figures and description are not intended to be restrictive.

Systems depicted in some of the figures may be provided in various configurations. Optionally, the systems may be configured as a distributed system where one or more components of the system are distributed across one or more networks in a cloud computing system. All features of the described systems are applicable to the described methods mutatis mutandis, and vice versa.

Figure 1:
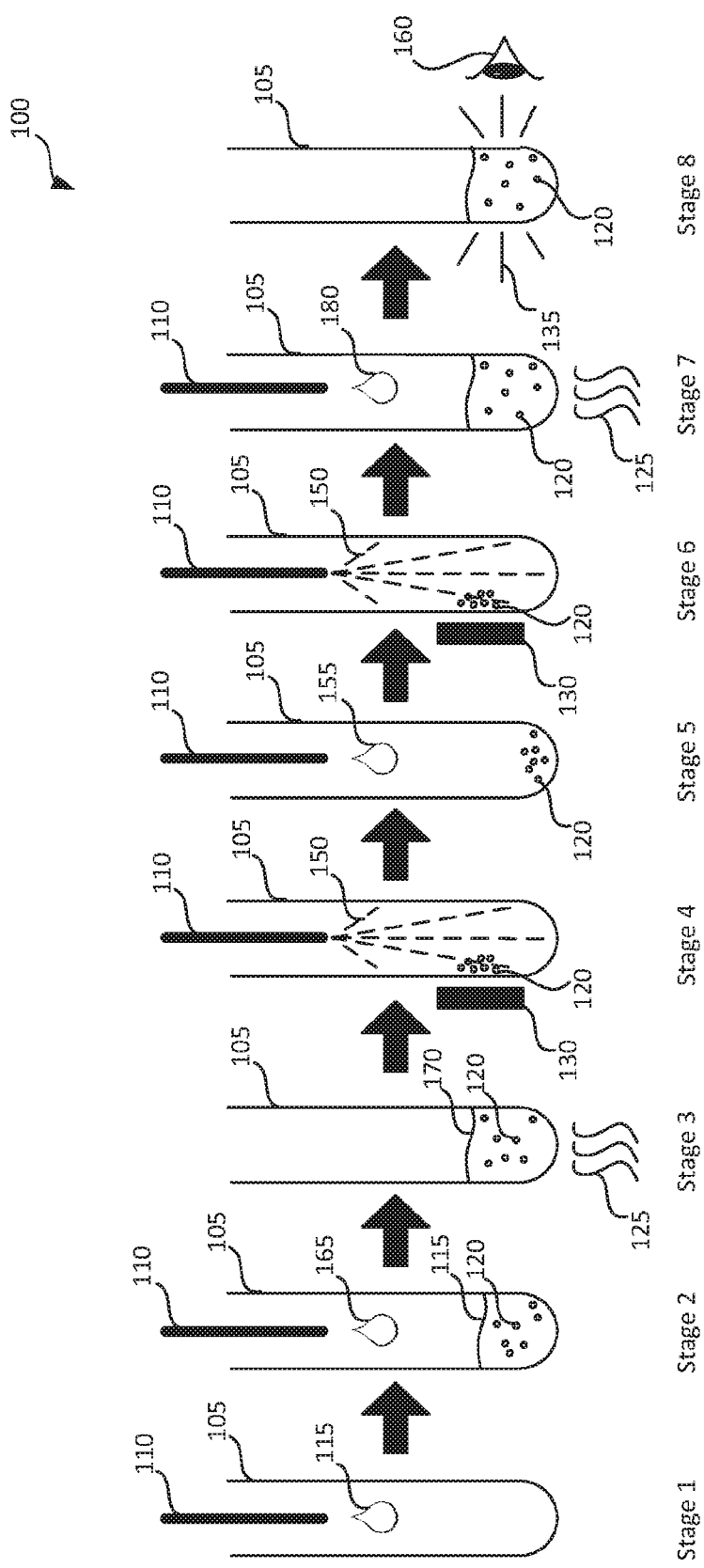
FIG. 1 is a schematic diagram that illustrates an example assay process that produces photons, according to an embodiment.

FIG. 1 illustrates an example assay 100. The example assay 100 may be performed using the methods and/or systems of the present disclosure. In addition, other assays may also use the methods and/or systems according to the principles of the present disclosure. The assay 100 begins at stage 1. Reaction vessel 105 (e.g., cuvette) can be used for the assay 100. A pipette 110 is used to place a first reagent 115 including iron particles 120 coated with antibodies or antigens into the reaction vessel 105. The first reagent 115 can include antibodies or antigens that are tailored to bond only with an analyte in a patient sample 165 that the assay is meant to measure. In assay 100, the iron particles 120 are coated with the antibodies or antigens.

At stage 2, the patient sample 165 is added to the reaction vessel 105 with pipette 110. Pipette 110 may be cleaned, new, or have a new tip at each stage. The patient sample 165 and the first reagent 115 are mixed.

At stage 3, the reaction vessel 105, containing the patient sample 165 and the first reagent 115 (including the iron particles 120) (i.e., mixture 170) are incubated with a heat source 125 to a predetermined temperature. During a binding process, the antibodies or antigens on the iron particles 120 of the first reagent 115 bind with the analyte of interest in the patient sample 165. The binding process can result in the analyte of the patient sample 165 binding with the antigens or antibodies that are coated on the iron particles 120.

At stage 4, the reaction vessel 105 is moved near one or more magnets 130, which attracts the iron particles 120 to one or more sides (e.g., perimeter portions) of the reaction vessel 105. Pipette 110 is used to wash the reaction vessel 105 with a washing agent 150. While washing, the magnet(s) 130 retain the iron particles 120 at the one or more sides of the reaction vessel 105. The iron particles 120 and the bound analyte of the patient sample 165 remain in the reaction vessel 105 after the washing is complete by virtue of the magnet(s) 130. Other components of the patient sample 165 may be absent from the reaction vessel 105 after the washing is complete, having been washed away by the washing agent 150.

At stage 5, a second reagent 155, including alkaline phosphatase ("ALP"), can be placed in the reaction vessel 105 with the iron particles 120 and the bound analyte of the patient sample 165 using pipette 110. The second reagent 155 and the iron particles 120 can be mixed and incubated. The second reagent 155 can include an antibody attached to the ALP that binds with the analyte of the patient sample 165, still attached to the iron particles 120.

At stage 6 the magnet(s) 130 pull the iron particles 120 to one or more sides of the reaction vessel 105. The iron particles 120 now have the bound analyte of the patient sample 165 and the ALP of the second reagent 155 bound to them. Unbound portions of the second reagent 155 are rinsed away with additional washing agent 150 added with pipette 110 to reaction vessel 105.

At stage 7, a substrate material 180 is added to the reaction vessel 105 with pipette 110. The substrate material 180 is mixed and incubated. The substrate material 180 reacts with the ALP enzyme and thereby produces light 135 (i.e., photons).

At stage 8, the light 135, emitted by the reaction of the substrate material 180 and the ALP attached to the iron particles 120, can be observed 160 (i.e., by processes that are sensitive to light). The observation 160 can be performed by a light detector (e.g., a PMT). The PMT can generate an output signal that can be processed to generate a relative light unit ("RLU") value (i.e., an output response) indicating a result of the assay 100. For example, a larger RLU value indicates more light, which indicates a larger amount of the analyte in the patient sample 165 than a smaller RLU value indicates.

Figure 2A:
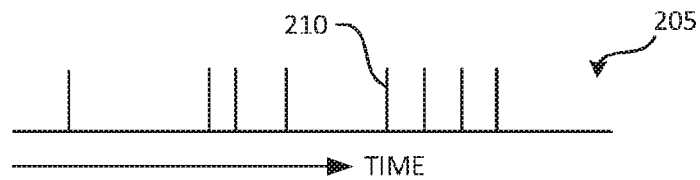
FIG. 2A is a graph that illustrates a representation of photon emission output over a period of time from an example assay that produces low photon levels, according to an embodiment.

FIG. 2A illustrates an example low photon emission input graph 205 depicting a low light level input to a PMT, according to an embodiment. Pulses 210 of low photon emission input graph 205 each indicate a single photon (e.g., emitted from the reaction of the ALP and the substrate material 180 of assay 100, described above). Low photon emission input graph 205 therefore indicates a plurality of single photoelectron emissions. Because the pulses 210 are sufficiently spaced in time, each of the single photon emissions is distinguishable and the individual photons can be counted by the PMT, as described further with respect to FIGS. 2C and 2E.

Figure 2B:
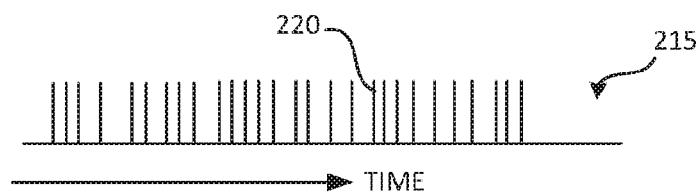
FIG. 2B is a graph that illustrates a representation of photon emission output over a period of time from an example assay that produces high photon levels, according to an embodiment.

FIG. 2B illustrates a high photon emission input graph 215, depicting a high light level input to a PMT, according to an embodiment. Pulses 220 each indicate a single photon (e.g., emitted from the reaction of the ALP and the substrate material 180 of assay 100, described above). High photon emission input graph 215 indicates multiple photoelectron emissions. In particular, individual photon emissions may become indistinguishable as they become closer in time, as described further with respect to FIGS. 2D. 2F, and 2G. High photon emission input graph 215 indicates the emission of photons at a higher light level than indicated at graph 205.

Figure 2C:
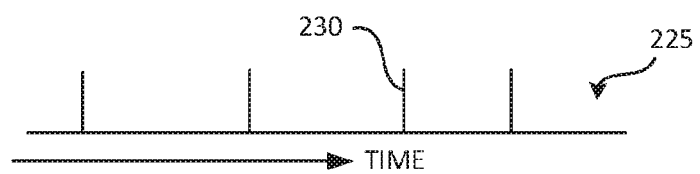
FIG. 2C is a graph that illustrates a representation of photoelectron emissions over a period of time within a photomultiplier tube ("PMT") receiving the example photon emission output illustrated at FIG. 2A.

FIG. 2C illustrates a low photoelectron emission graph 225 depicting individual photoelectron emission that is measureable within a PMT using the photons indicated by pulses 210 of low photon emission input graph 205 as the input (i.e., measured photons). Individual photons received by the PMT may each result in an emission of an individual photoelectron within the PMT. Each pulse 230 indicates a single photoelectron ejected by a photon. Not every emitted photon is measurable and/or within a readable view of an aperture of the PMT. Accordingly, not every photon indicated by pulses 210 of low photon emission input graph 205 is counted by the PMT.

Figure 2D:
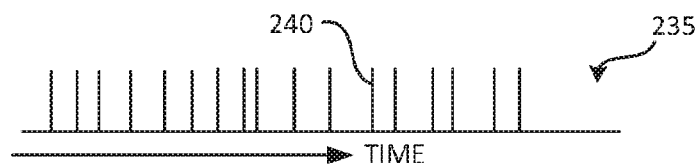
FIG. 2D is a graph that illustrates a representation of photoelectron emissions over a period of time within a PMT receiving the example photon emission output illustrated at FIG. 2B.

FIG. 2D illustrates high photoelectron emission graph 235, which represents the photoelectron emission that is measurable within the PMT using the photons indicated by pulses 220 of high photon emission input graph 215 as the input (i.e., measured photons). Because not every photon is measurable and/or within the readable view of the aperture of the PMT, the photoelectron emission graph 235 does not depict a photoelectron (indicated by pulses 240) for every photon indicated by a pulse 220 in the high photon emission input graph 215.

Figure 2E:
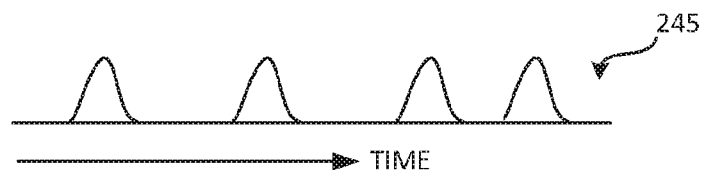
FIG. 2E is a graph that represents an example signal output response of the PMT with the example photoelectron emission illustrated at FIG. 2C, the example signal output response having discreet pulses, according to an embodiment.

FIG. 2E illustrates a discreet signal output response graph 245 depicting the discrete pulse signal output of the PMT. Discreet signal output response graph 245 illustrates that the discrete pulses each have a time duration including a ramp-up portion and a ramp-down portion. Discreet signal output response graph 245 may be the signal output response of the PMT with the example photoelectron emission illustrated in low photoelectron emission graph 225. The range of RLUs readable by the PMT using a discrete pulse mode has an upper threshold, which varies for each PMT. For example, the upper threshold may be up to approximately 12 million to 14 million RLLUs. Because the discrete pulses of discreet signal output response graph 245 are separated in time, the pulses can be distinguished from each other and individual photon counting is possible.

Figure 2F:
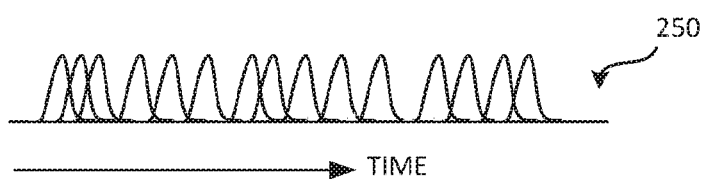
FIG. 2F is a graph that represents an example signal output response of the PMT with the example photoelectron emission illustrated at FIG. 2D, the example signal output response having overlapping pulses, according to an embodiment.

FIG. 2F illustrates overlapping pulse signal output response graph 250, which represents the discrete pulse signal output of the PMT when the input optical power is too high to read all of the discreet pulse signals. Overlapping pulse signal output response graph 250 illustrates that the discrete pulses each have a time duration including a ramp-up portion and a ramp-down portion, and the ramp-up and ramp-down portions overlap the neighboring pulses. Overlapping pulse signal output response graph 250 may be the signal output response of the PMT with the example photoelectron emission illustrated in high photoelectron emission graph 235. Because the discrete pulses are not cleanly separated in time, they cannot always be distinguished from each other and pulse counting is not possible without losing a significant number of pulses in the count.

Figure 2G:
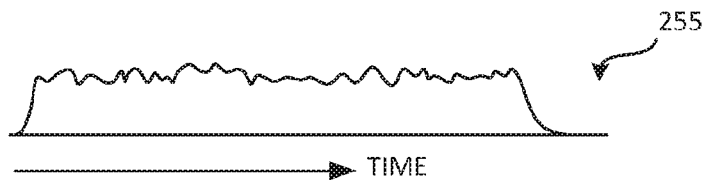
FIG. 2G is a graph that represents an example signal output response of the PMT with an example high-rate photoelectron emission, the example signal output response depicted with overlapped pulses, according to an embodiment.

FIG. 2G illustrates overlapped signal output response graph 255, which represents the pulse overlapped signal output of the PMT with the example photoelectron emission illustrated in a high photoelectron emission graph. The pulse overlapped signal output can be measured by an electrical current (i.e., amperage) output of the PMT, and an RLU value can be generated according to embodiments described herein.

As shown in FIGS. 2A-2G, at lower input light levels (i.e., light levels generating an output response below the discreet/analog crossover), a vast majority of the discrete pulses of the photoelectrons can be distinguished, and an output response RLU value can be accurately determined based on individual photon counting. At higher input light levels (i.e., light levels generating an output response above the discreet 1 analog crossover), many of the discrete pulses of the photoelectrons cannot be distinguished, and an output response RLU value cannot be accurately determined based on individual photon counting. At higher light levels, the analog current output of the PMT can be measured, can be converted to a voltage that is measured, and/or otherwise processed as a signal to determine the RLU output, as described further herein.

Figure 3:
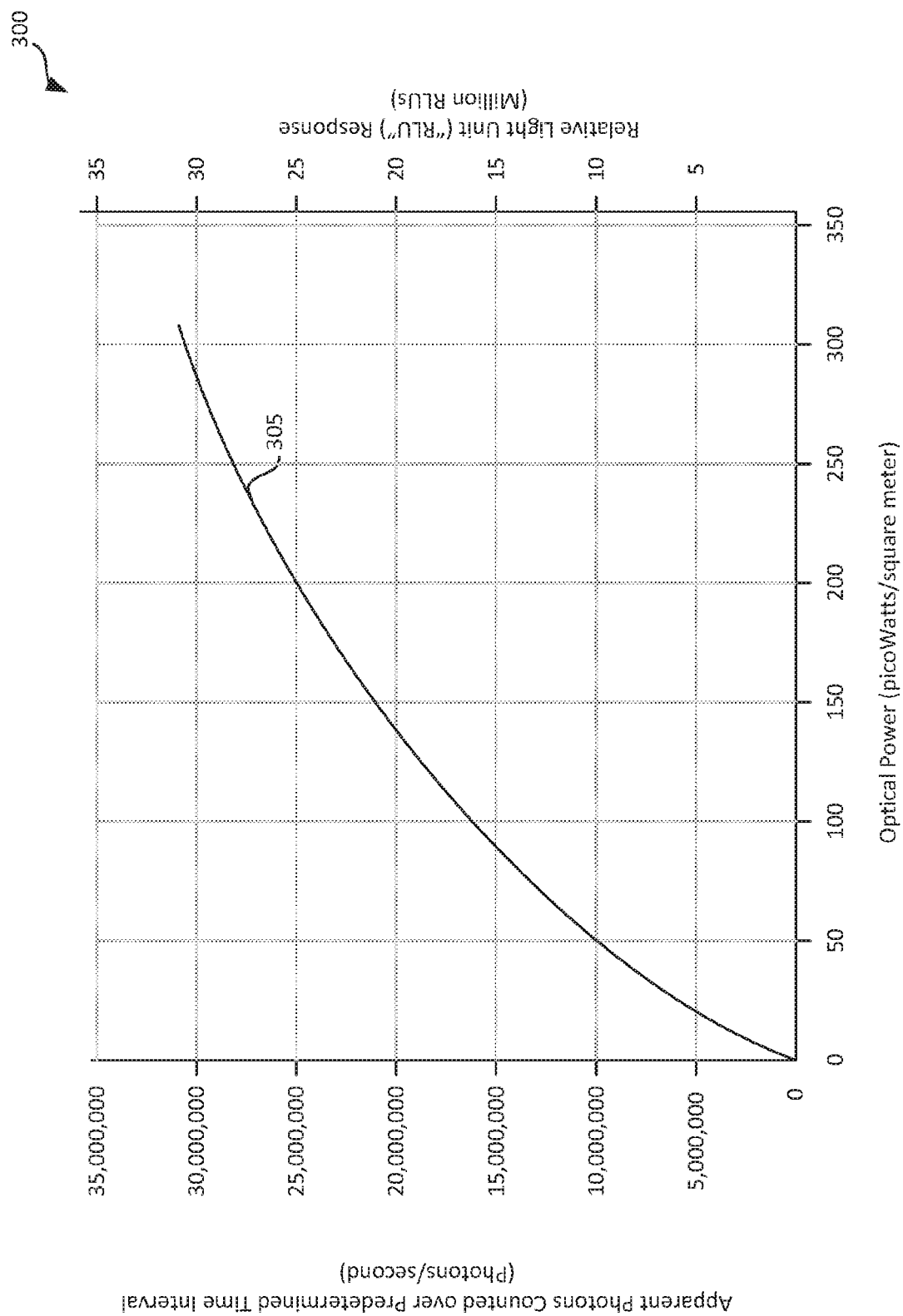
FIG. 3 is an example graph of a prior art PMT output response in relation to input optical power.

FIG. 3 illustrates an example graph 300 of an output response of a prior art luminometer with a typical PMT. The example graph 300 depicts the RLU output response of the luminometer with respect to input optical power. A PMT outputs a signal having a discreet component. The discreet component provides a signal representing a discreet photon count. As the photon rate increases, an increasing number of counts are lost because of pulse overlap, as described above. Luminometers include electrical hardware and circuitry to obtain the PMT output signal and convert the output signal into an RLU output response. In the prior art luminometer, illustrated by the example graph 300, the relationship between the RLU output response of the luminometer and the input optical power is non-linear. As seen by graph 300, with the prior art luminometer, as the optical power increases, the RLU output response of the luminometer becomes non-linear as more photon counts are missed, which results in curve 305, which is non-linear. Photons cannot be individually counted at higher light levels (i.e., higher optical power) without missing a substantial number of photon counts because the PMT is unable to detect individual photons whose pulses substantially overlap in time. This is shown by high photon emission input graph 215, high photoelectron emission graph 235, overlapping pulse signal output response graph 250, and overlapped signal output response graph 255. Further, each PMT is calibrated in one of multiple ways, each of which may impact the RLU output of the PMT at higher light levels. For example, graph 300 is an example output response from an Access 2, DxI 600, or DxI 800.

Figure 4:
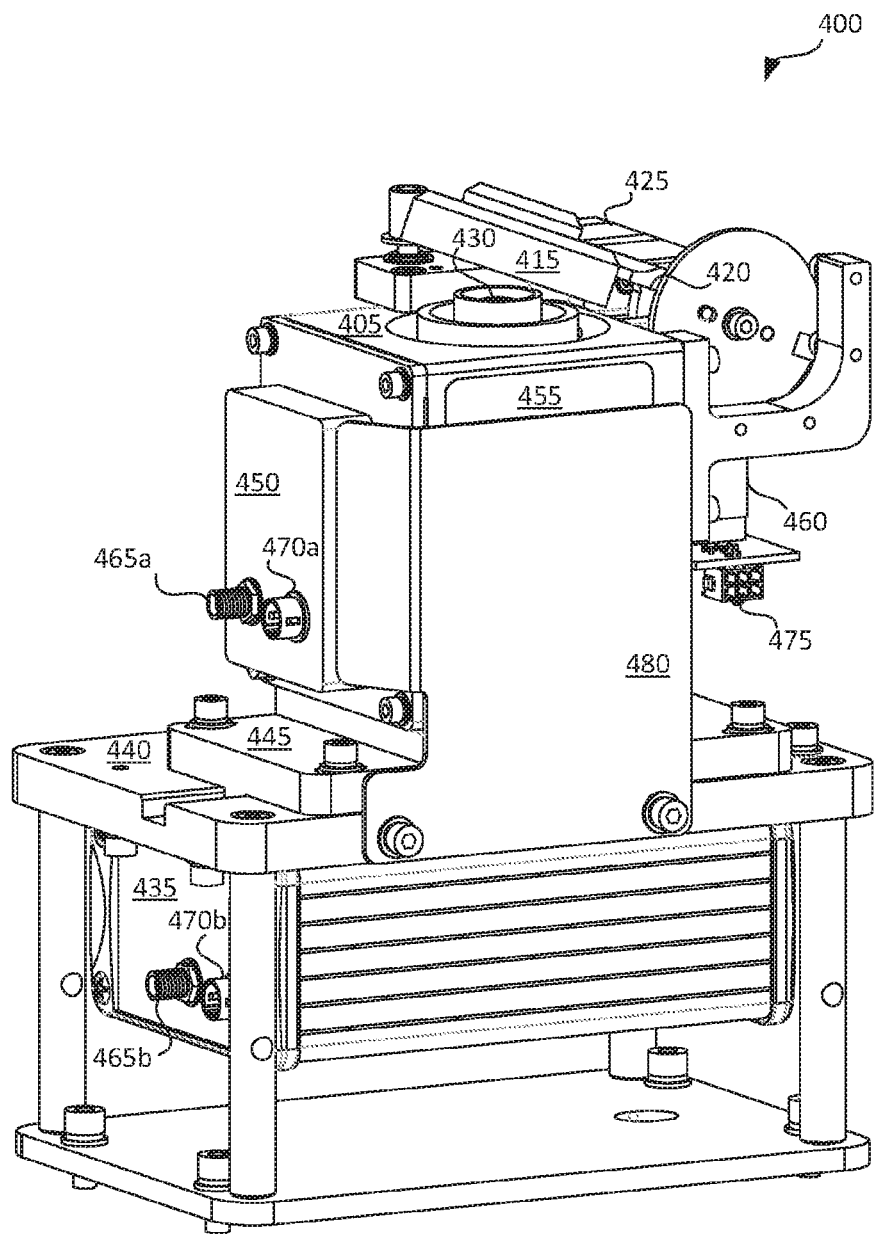
FIG. 4 is a perspective view illustrating an example luminometer for performing an assay, according to an embodiment.

FIG. 4 illustrates a perspective view of a luminometer 400 for performing an assay 100, according to an embodiment. Luminometer 400 mitigates increasing inaccuracies at higher input optical power as well as other inaccuracies including photon contamination, reaction vessel position inaccuracies, and thermal variances. FIG. 4 provides an external view of luminometer 400.

Luminometer 400 includes a chassis 405. In certain embodiments, the chassis 405 can be any material that promotes thermal and electrical conductance and thermal consistency, such as, for example, aluminum. The chassis 405 includes a chassis portion 535 of a labyrinth seal 530 depicted in more detail in FIGS. 5B, 7A. 7B, and 7C. At the center of the chassis portion 535 of the labyrinth seal 530 is a chamber opening 430 providing access to a reaction vessel chamber 610 (see FIG. 7B).

Luminometer 400 includes a cap 415. The cap 415 can be the same material as the chassis 405, such as, for example aluminum. As a more specific example, 6061-T6 aluminum can be used for aluminum portions of the luminometer 400 including the cap 415 and the chassis 405. The cap 415 can form a non-contacting photon seal when closed over the chassis portion 535 of the labyrinth seal 530 of the chassis 405 and thereby form a dark chamber 545 (see FIG. 7C). Stated differently, the cap 415 can be placed over the chassis portion 535 of the labyrinth seal 530 of the chassis 405 to restrict external light (light emitted from external sources) from entering the reaction vessel chamber 610. Optionally, a cap portion 540 of the labyrinth seal 530 (shown in more detail in FIGS. 5B, 7A, and 7C), which is included on the cap 415, does not make physical contact with the chassis portion 535 of the labyrinth seal 530. Optionally, the cap 415 can be considered closed (i.e. in a closed state or closed configuration 555) when external light entering the reaction vessel chamber 610 is restricted sufficiently that a PMT 630 does not measure external light (i.e., light introduced within the reaction vessel chamber 610 by a source outside of chassis 405 and/or calibration unit 460). The labyrinth seal 530 may be made of and/or coated with light absorbing material. For example, the cap portion 540 of the labyrinth seal 530 and/or the chassis portion 535 of the labyrinth seal 530 may absorb light. Thus, even though the labyrinth seal 530 may be non-contacting, light may not reflect within clearances of the labyrinth seal 530 to reach the reaction vessel chamber 610 when the labyrinth seal 530 is in the closed configuration 555. When a bottom 685 of the cap 415 is parallel to (even though optionally not contacting) a top 680 of the chassis 405 and the chassis portion 535 of the labyrinth seal 530, and the cap portion 540 and the chassis portion 535 of the labyrinth seal 530 engage due to the intermeshing walls, the cap 415 is in a closed configuration 555. The cap 415 can be lifted and lowered by a cap arm 420, as described in further detail below. Once an opening angle 655 (see FIG. 6B) between the bottom 685 of the cap 415 and the top 680 of the chassis 405 reaches approximately 7 degrees or more, the cap 415 enters an open configuration 560 (i.e., the cap 415 is open or in an open state). As depicted in FIG. 4, the cap 415 is in an open configuration 560. Upon the opening angle 655 of the cap 415 reaching a sufficient angle (e.g., 90 degrees), a chamber opening 430 to the reaction vessel chamber 610 is accessible by, for example, a pick-and-place unit 790 (see FIG. 7D) which may deliver a reaction vessel 105 to the reaction vessel chamber 610 and/or retrieve the reaction vessel 105 from the reaction vessel chamber 610. An example gripper assembly that is suitable for use with the pick-and-place unit 790 is illustrated at U.S. Pat. No. 7,128,874 B2, incorporated herein by reference in its entirety.

The cap arm 420 can cause the cap 415 to open and close. The cap arm 420 can be controlled (i.e., actuated) by an actuator 425 (e.g., a motor 425). As depicted, the actuator 425 is a stepper motor 425.

Luminometer 400 can include a computer system 1500 that is configured as a luminometer controller 905 and a luminometer computer system compartment 435. The luminometer computer system compartment 435 can house the computer system portion of the luminometer 400 that is described in more detail with respect to FIG. 9A.

The luminometer 400 can include a sensor (not shown) that can detect whether the cap 415 is closed or open and/or is entering a closed state or entering an open state. The cap sensor can send a signal to the luminometer controller 905 (within luminometer computer system compartment 435) that can register the sensor signal and, when the cap 415 is entering an open state or is open (i.e., is in an open configuration 560), send a signal to close a shutter 660 to protect the PMT 630 in the luminometer 400 from damage due to light entering the reaction vessel chamber 610 through the chamber opening 430. When the cap 415 is entering a closed state 555 or is closed, the sensor can send a signal to the luminometer controller 905. The luminometer controller 905 can register the signal and open the shutter 660 to allow the PMT 630 to view light sources within the light passage 640 and the reaction vessel chamber 610 (i.e., the dark chamber 545). The shutter 660 can be an electronic shutter 660 such that it automatically opens and closes upon receiving the signal from the sensor. The shutter 660 can be a solid state electronic shutter 660 (i.e., no moving parts).

Luminometer 400 can include a stand 440 for supporting the chassis 405, the computer system compartment 435, and the other components of luminometer 400. A thermal barrier 445 can separate the chassis 405 from the stand 440. As depicted, the thermal barrier 445 also serves as a position adjustment for the luminometer 400 (e.g., to align the reaction vessel chamber 610 with the pick-and-place unit 790). In other embodiments, the thermal barrier 445 may be separate from the pick-and-place unit 790. Stated differently, a thermal barrier 445 can be placed on the stand 440 and the chassis 405 can be placed on the thermal barrier 445. The thermal barrier 445 can be plastic to mitigate thermal transfer between the chassis 405 and the stand 440 as well as between the chassis 405 and the luminometer computer system compartment 435.

Luminometer 400 can include a PMT cover 450 that can be any material that promotes thermal and electrical conductance and thermal consistency, such as, for example, aluminum (e.g., 6061-T6 aluminum). The PMT cover 450, assembled to a housing 410 of the chassis 405, can form an enclosure 565 (see FIG. 7C) that houses the PMT 630. The enclosure 565 can mitigate thermal transfer between the chassis 405 and the external environment. A heating element 455 (e.g., a heating blanket) can surround the chassis 405 and be controlled by a thermistor (not shown) within a thermistor passage (also called a thermistor channel) in the chassis 405. The thermistor can measure a temperature of the chassis 405 and/or the enclosure 565. In other embodiments, any temperature sensor may be used in place of or together with the thermistor. The thermistor can transmit a temperature signal that can be sent to the luminometer controller 905 of the luminometer 400 which can maintain a constant temperature of the chassis 405 and/or the enclosure 565 by turning the heating element 455 on when the temperature falls and turning the heating element 455 off when the temperature reaches a predetermined set point. A constant temperature within the chassis 405 can mitigate thermal variance discrepancies (i.e., inaccuracies) with the assay results. An optimal constant temperature can be, for example, 37 degrees Celsius. Luminometer 400 can further include heating element cover 480. Heating element cover 480 can help discourage thermal transfer to the external environment from heating element 455. The PMT cover 450 can be coupled to the chassis 405 with a conductive gasket 485 (see FIGS. 6A and 7C). The conductive gasket 485 can promote electromagnetic interference shielding within the chassis 405 and/or the enclosure 565 as well as promoting thermal consistency in luminometer 400. The conductive gasket 485 can provide thermal conductivity as well as electrical conductivity between the chassis 405 and the PMT cover 450. The chassis 405 and the PMT cover 450 can create a thermal cavity defining an enclosed volume that houses the PMT 630, the reaction vessel chamber 610, and the light passage 640. The cavity and the dark chamber 545 can thus be free of external light, at a constant temperature, and shielded from electromagnetic interference.

Luminometer 400 can also include a calibration unit 460 (e.g., an on-board calibration unit 460). The calibration unit 460 can be used to calibrate the PMT 630, as described with respect to FIGS. 9A, 11, and 14. The calibration unit 460 can have a receptacle 475 for providing power input to the calibration unit 460 and signal output from the calibration unit 460. The signal output of the calibration unit 460 can be transmitted to the luminometer controller 905 in luminometer computer system compartment 435.

Luminometer 400 can also include a PMT voltage input socket 470a which is coupled to a PMT voltage input socket 470b and provides power input to the PMT 630. Luminometer 400 can also include a luminometer output signal socket 465a which is coupled to a luminometer output signal socket 465b. The PMT voltage input socket 470a and the PMT voltage input socket 470b can be coupled with a cable that allows a voltage power to be sent from the luminometer computer system compartment 435 to the PMT 630 for powering the PMT 630. The luminometer output signal socket 465a and the luminometer output signal socket 465b can be coupled with a cable that allows the output signal of the PMT 630 to be sent from the PMT 630 to the luminometer computer system in the luminometer computer system compartment 435. While PMT voltage input socket 470a and luminometer output signal socket 465a are shown placed horizontally next to each other at FIGS. 4, 5A, and 6A, other configurations and locations for the sockets 470a and 465a are within the scope of this disclosure (e.g., at FIGS. 6B and 7C).

Figure 5A:
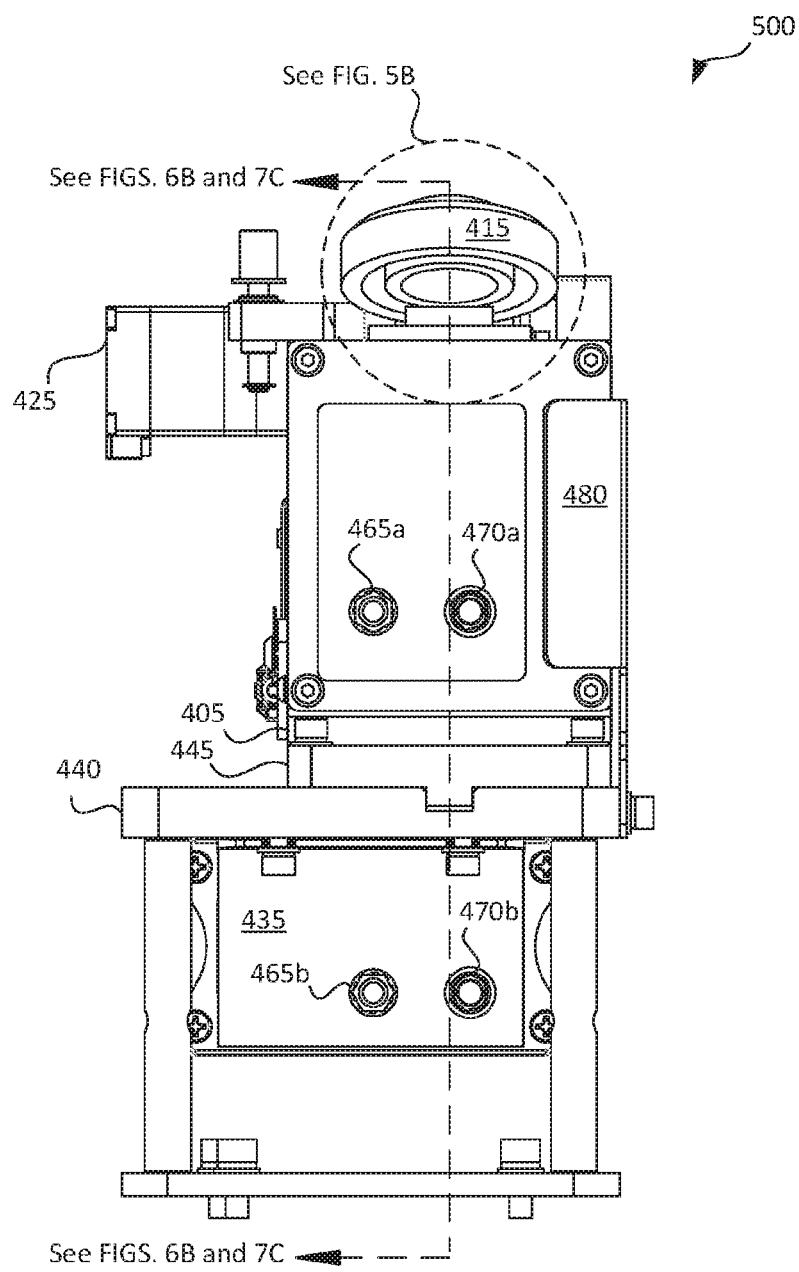
FIG. 5A is a front elevation view illustrating the example luminometer of FIG. 4, according to an embodiment.

FIG. 5A illustrates a front elevation view 500 of the luminometer 400, according to an embodiment. The front elevation view 500 depicts the cap 415, the chassis 405, the luminometer computer system compartment 435, the stand 440, the motor 425, the heating element cover 480, and the thermal barrier 445. Also shown is the PMT voltage input socket 470a, the PMT voltage input socket 470b, the luminometer output signal socket 465a, and the luminometer output signal socket 465b. The side view 500 also shows both the cap portion 540 of the labyrinth seal 530 and the chassis portion 535 of the labyrinth seal 530. As shown by the dashed circle, an enlarged portion of the front elevation view of the labyrinth seal 530 is provided in FIG. 5B.

Figure 5B:
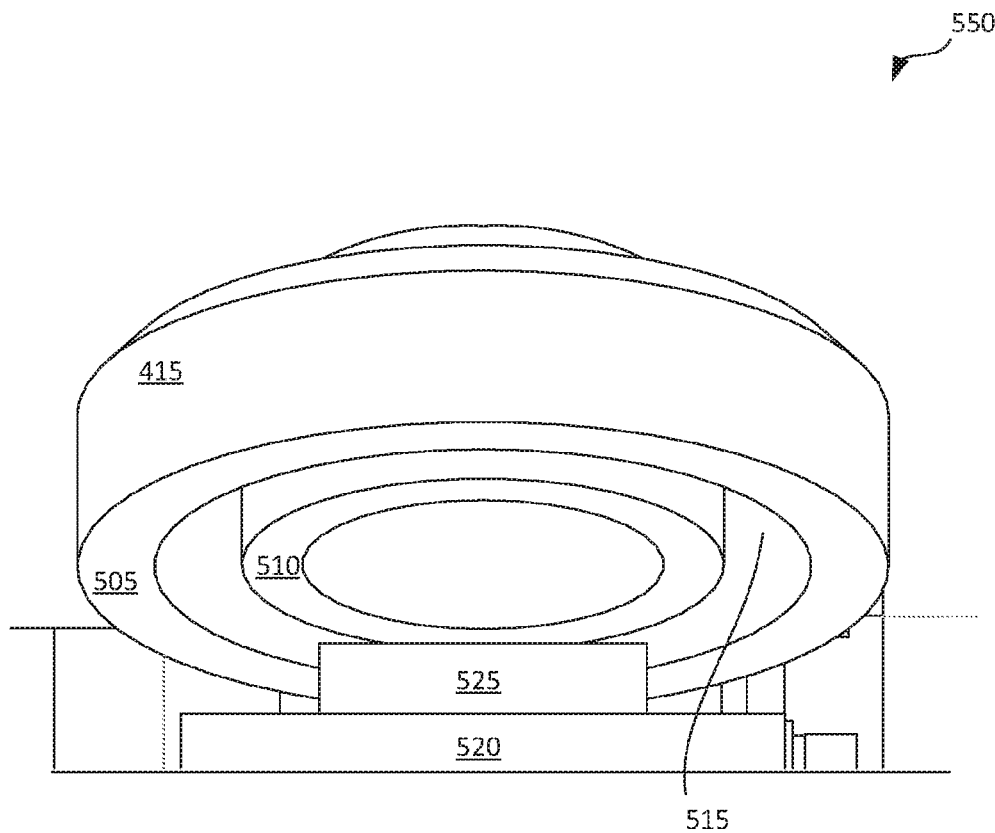
FIG. 5B is an enlarged portion of FIG. 5A, as called out at FIG. 5A.

FIG. 5B illustrates an enlarged view 550 of the labyrinth seal 530 formed by the cap portion 540 of the labyrinth seal 530 and the chassis portion 535 of the labyrinth seal 530. The cap portion 540 of the labyrinth seal 530 is included with the cap 415. Between a cap outer concentric ring 505 (i.e., a wall) and a cap inner concentric ring 510 (i.e., a wall) is a cap trough 515 (i.e., a wall receiver). The cap outer concentric ring 505, cap inner concentric ring 510, and trough 515 form the cap portion 540 of the labyrinth seal 530. The chassis portion 535 of the labyrinth seal 530 includes a chassis outer concentric ring 520 (i.e., a wall), a chassis inner concentric ring 525 (i.e., a wall), a chassis inner trough 725 (i.e., a wall receiver and a chassis outer trough 730 (i.e., a wall receiver). Chassis inner concentric ring 525 is the innermost (i.e., centermost) ring and may be taller than the chassis outer concentric ring 520. As depicted, the chassis inner concentric ring 525 is a circular wall and having a larger height can facilitate exclusion of light in the reaction vessel chamber 610 even when the bottom 685 of the cap 415 is not parallel with the top 680 of the chassis 405. The external diameter (i.e., the diameter of the outermost edge) of the chassis inner concentric ring 525 is larger than the diameter of the chamber opening 430 allowing access to the reaction vessel chamber 610. Between the chassis inner concentric ring 525 and chassis outer concentric ring 520, there is a chassis inner trough 725 that has an external diameter larger than the external diameter of the chassis inner concentric ring 525. Outside the chassis outer concentric ring 520 (which has an external diameter larger than the external diameter of the chassis inner trough 725), there is a chassis outer trough 730 that has an external diameter larger than the external diameter of the chassis outer concentric ring 520. The cap portion 540 of the labyrinth seal 530 can engage with (i.e., mesh with) the chassis portion 535 of the labyrinth seal 530 when in a closed configuration 555 (see FIG. 7C). When closed, the cap trough 515 can fit over the chassis outer concentric ring 520 of the chassis portion 535 of the labyrinth seal 530. The cap trough 515 can have an external diameter that is larger than the external diameter of the chassis outer concentric ring 520. The cap inner concentric ring 510 can fit within chassis inner trough 725 and the cap outer concentric ring 505 can fit within chassis outer trough 730.

Figure 6A:
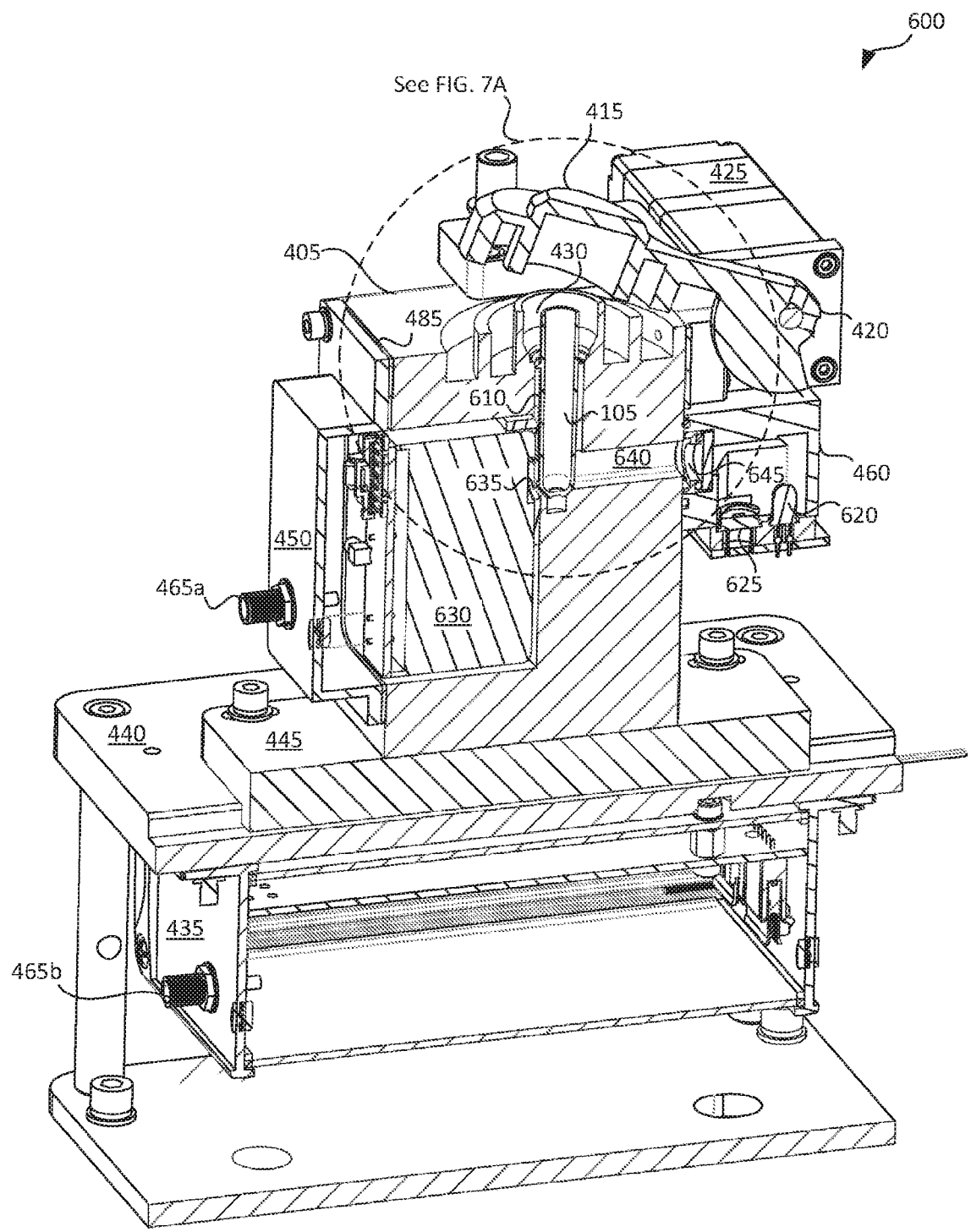
FIG. 6A is a cross-sectional perspective view illustrating the example luminometer of FIG. 4, according to an embodiment.
Figure 7A:
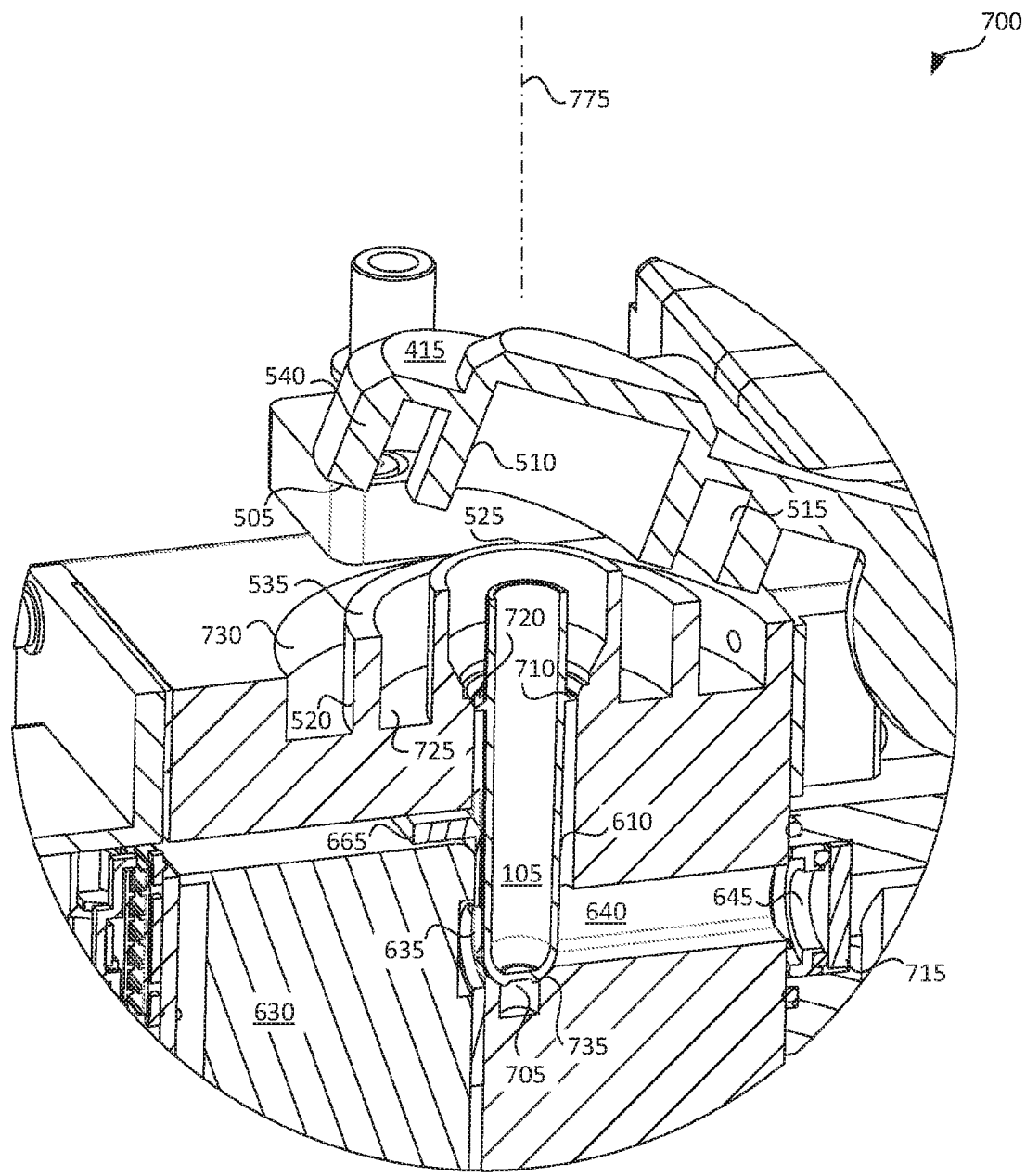
FIG. 7A is an enlarged portion of FIG. 6A, as called out at FIG. 6A.

FIG. 6A illustrates a cross-sectional perspective view 600 of the luminometer 400 for performing the assay 100, according to an embodiment. The cross-sectional perspective view 600 provides a cut-away view of luminometer 400 as shown by the cross-sectional cutting line in FIG. 5A. The cut portions of the cross-sectional perspective view 600 are shown by cross-hatching. The cross-sectional perspective view 600 illustrates the cap 415, the chassis 405, the luminometer computer system compartment 435, the PMT cover 450, the stand 440, the motor 425, the thermal barrier 445, and the calibration unit 460. Also shown is the luminometer output signal socket 465a and the luminometer output signal socket 465b. As indicated by the dashed circle, FIG. 7A provides an enlarged view of a portion of the cross-sectional perspective view 600 of the luminometer 400.

The cross-sectional perspective view 600 provides a view of the chamber opening 430, which provides access to reaction vessel chamber 610. Reaction vessel 105 is shown seated within reaction vessel chamber 610. Light passage 640 intersects with reaction vessel chamber 610 near the bottom of the reaction vessel chamber 610.

The cross-sectional perspective view 600 further provides a view of the PMT 630. The PMT 630 can be a photomultiplier tube or any other suitable light detecting device or light detector. The PMT 630 can include a sensing element (not shown in detail) that detects light from light passage 640 and/or the reaction vessel chamber 610. The PMT 630 is adjacent an aperture 635 that is aligned with the light passage 640 and past an intersection of the light passage 640 and the reaction vessel chamber 610. The aperture 635 allows light to enter the PMT 630 and the sensing element to receive the light. The reaction vessel chamber 610 intersects with the light passage 640 such that when the reaction vessel 105 is placed in the reaction vessel chamber 610, the substance or sample within the reaction vessel 105 can emit photons viewable in the light passage 640 and to the aperture 635. The aperture 635 can be limited in size, for example to 8.5 centimeters in diameter, to limit the view of a meniscus 815 within the reaction vessel 105 as discussed in more detail with respect to FIG. 8. On the other end of the light passage 640, the calibration unit aperture 645 can align with the light passage 640. The calibration unit 460 can include a light emitting diode ("LED") 620 and a photodiode 625. The LED 620 and photodiode 625 can provide a regulated internal light source used to calibrate PMT 630. The reaction vessel 105 is not needed in the luminometer 400, for example during calibration. While the luminometer 400 is described as including the reaction vessel 105, this is an optional component of the system that may not necessarily be part of the luminometer 400.

Figure 6B:
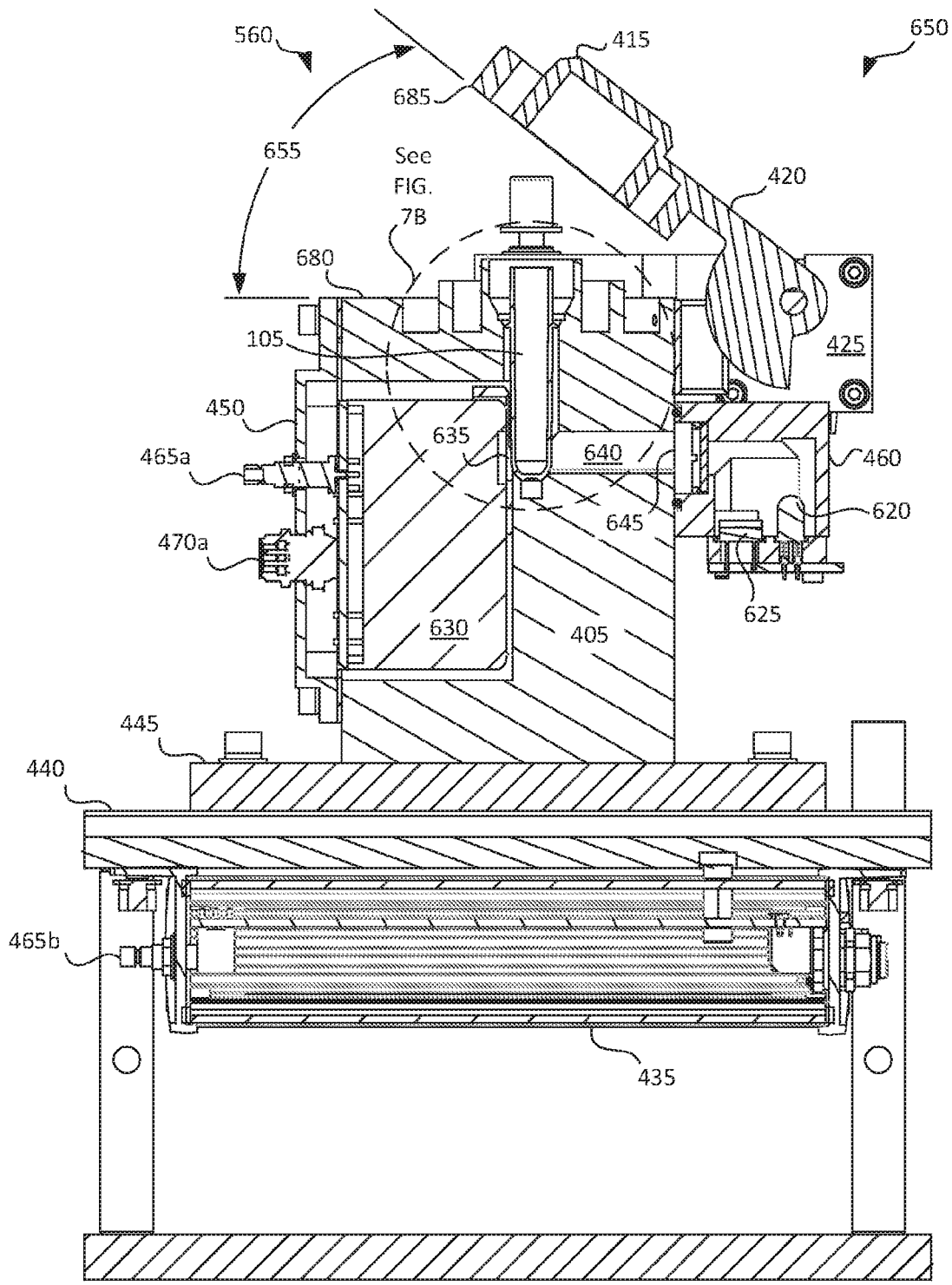
FIG. 6B is a cross-sectional side elevation view, as called out at FIG. 5A, illustrating the example luminometer of FIG. 4, according to an embodiment.
Figure 7B:
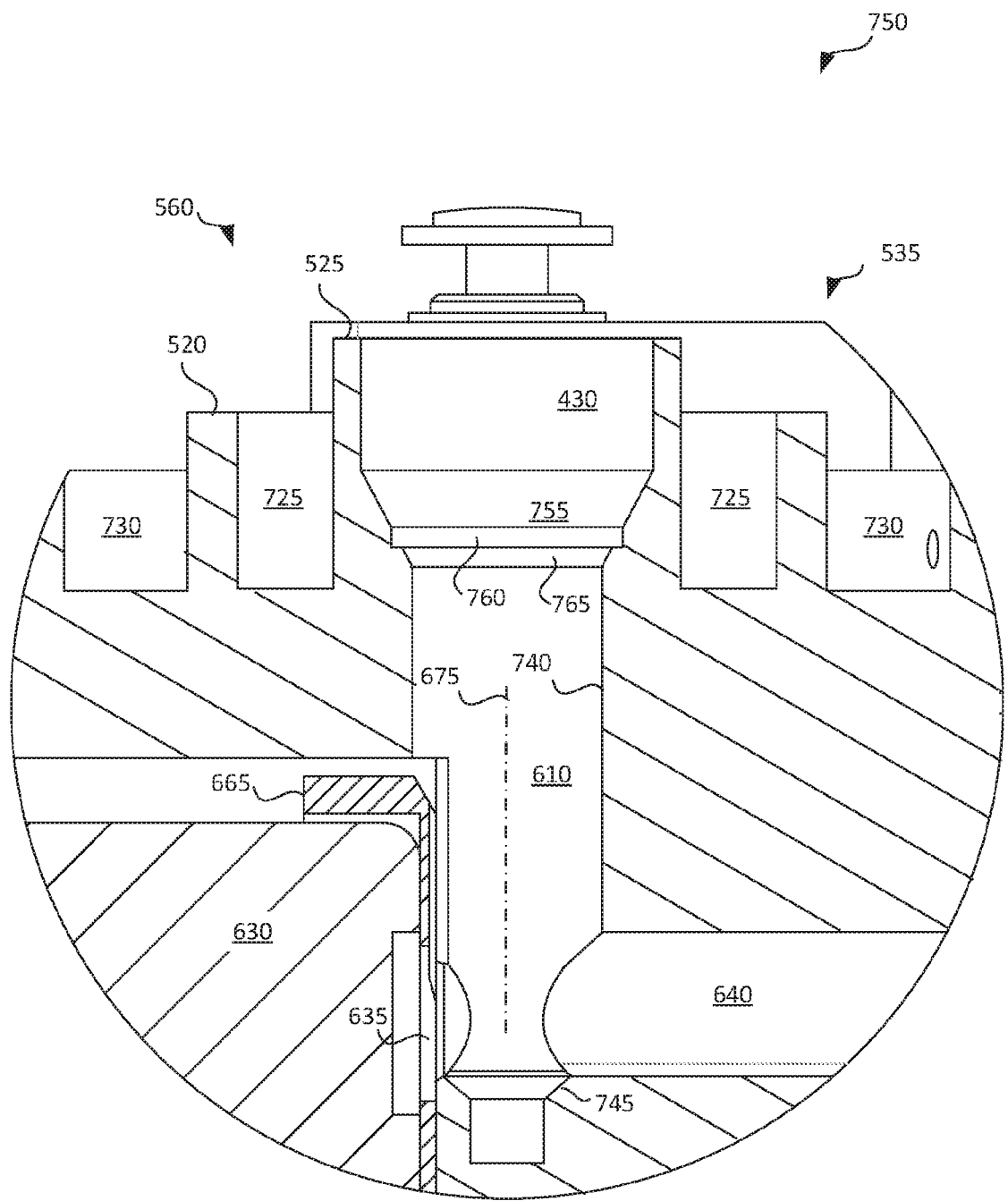
FIG. 7B is an enlarged portion of FIG. 6B, as called out at FIG. 6B, but with a reaction vessel removed.

FIG. 6B illustrates across-sectional side elevation view 650 of luminometer 400 for performing the assay 100. The cross-sectional side elevation view 650 provides a cut-away view as thought the luminometer 400 were cut by the cross-sectional cutting line in FIG. 5A. The cut portions of the cross-sectional side view 650 are shown by cross-hatching. The cross-sectional side view 650 depicts the cap 415, the chassis 405, the cap arm 420, the motor 425, the luminometer computer system compartment 435, the PMT cover 450, the stand 440, the motor 425, the thermal barrier 445, and the calibration unit 460. Also shown are the luminometer output signal socket 465a and the luminometer output signal socket 465b. As indicated by the dashed circle, FIG. 7B provides an enlarged portion of the cross-sectional side view 650 of the luminometer 400.

Cross-sectional side elevation view 650 indicates that opening angle 655 is the angle between a bottom 685 of the cap 415 and the top 680 of the chassis 405. As the cap 415 moves toward the closed configuration 555, the opening angle 655 becomes smaller. Once the opening angle 655 reaches approximately seven degrees or less, the cap 415 is in a closed configuration. When the cap 415 is in a closed configuration 555, a dark chamber 545 is formed within reaction vessel chamber 610. The dark chamber 545 is formed when no external light (i.e., light from light sources external to chassis 405) can enter the dark chamber 545. The dark chamber 545 includes the light passage 640 and the reaction vessel chamber 610.

The cross-sectional side elevation view 650 further provides another view of the PMT 630. As shown in this cross-sectional side elevation view 650, the light passage 640 intersects with reaction vessel chamber 610 on one end.

On the other end, the light passage 640 is coupled to the calibration unit 460. The calibration unit 460 can include the LED 620 and the photodiode 625. The calibration unit aperture 645 allows light from the calibration unit 460 to pass into the light passage 640.

FIG. 7A illustrates an enlarged partial perspective view 700 of the cross-sectional perspective view 600 of the luminometer 400 for performing the assay 100, according to an embodiment. The enlarged perspective view 700 is identified by the dashed circle in cross-sectional perspective view 600 of FIG. 6A. Shown in enlarged perspective view 700 are cap 415 with cap outer concentric ring 505, cap inner concentric ring 510, and cap trough 515 to form the cap portion 540 of the labyrinth seal 530. Further shown in enlarged perspective view 700 is the chassis portion 535 of the labyrinth seal 530 formed by chassis outer concentric ring 520, chassis inner concentric ring 525, chassis outer trough 730, and chassis inner trough 725. Enlarged perspective view 700 further depicts reaction vessel 105, reaction vessel chamber 610, PMT 630, aperture 635, calibration unit aperture 645, and light passage 640.

Enlarged perspective view 700 shows additional detail of calibration unit 460, including filter 715, which may cover calibration unit aperture 645. Filter 715 can filter the light emission from LED 620 into light passage 640.

Enlarged perspective view 700 shows additional detail of reaction vessel chamber 610 and reaction vessel 105. A kinematic spherical joint 705 is depicted. The kinematic spherical joint 705 can include a first portion 745 (see FIG. 7B) that is a partial sphere, a cone, a partial cone, or other functional geometry that is located at, adjacent, or toward the bottom of the reaction vessel chamber 610. The reaction vessel 105 can include a second portion 735 of the kinematic spherical joint 705 that may be a convex spherical nose that mates to the first portion 745 of the kinematic spherical joint 705. As depicted, the second portion 735 includes a partial spherical nose. The kinematic spherical joint 705 can limit three degrees of freedom of the reaction vessel 105 (i.e., three mutually orthogonal directions of a point centered at the second portion 735). Additionally, the reaction vessel 105 can have a first portion 710 of a kinematic cylindrical joint 720 that is a fin 710 that fits within a second portion 740 of the kinematic cylindrical joint 720. As depicted in FIG. 7B, the second portion 740 is a cylindrical feature of the reaction vessel chamber 610 and defines an axis 675. In other embodiments, other geometry may be used. The kinematic cylindrical joint 720 is formed by the second portion 740 in conjunction with the fin 710 and can limit two additional degrees of freedom of the reaction vessel 105 (i.e., two mutually orthogonal rotational directions about the point centered at the second portion 735). The only remaining degree of freedom is vertical axial rotation about an axis 775 of symmetry of the reaction vessel 105. For the purposes of the assay 100 in luminometer 400, vertical axial rotation will not impact the assay 100, and therefore need not be limited. The second portion 740 of the reaction vessel chamber 610 can be sized such that the clearance between an outer diameter of the fin 710 of the reaction vessel 105 and the inner diameter of the second portion 740 of the reaction vessel chamber 610 is very small, for example, less than 0.001 inch. The fin 710 may be spaced less than a fin thickness from (i.e., below) the tapered portion 765 of the reaction vessel chamber 610. The outer diameter of the fin 710 can be, for example, 10.182 millimeters+/−0.16 millimeter. The outer diameter of the fin 710 can interface with the second portion 740 of the kinematic cylindrical joint 720 that can be, for example, 10.414 millimeters+/−0.12 millimeter in inner diameter. The sizing can provide clearance for the fin 710 to facilitate removal of the reaction vessel 105 from the reaction vessel chamber 610. A clearance groove 760 may facilitate the insertion of a collet 795 of the pick-and-place 790 unit into the chamber opening 430. A tapered portion 755 may guide the collet 795 as it positions the reaction vessel 105 into the reaction vessel chamber 610. The tapered portion 765 may guide the outer diameter of the fin 710 as the reaction vessel 105 is positioned into the reaction vessel chamber 610. The tapered portions 755 and 765 prevent binding when the reaction vessel 105 (and the collet 795) is removed from the reaction vessel chamber 610.

FIG. 7B illustrates an enlarged partial side view 750 of the cross-sectional side elevation view 650 of the luminometer 400 for performing the assay, according to an embodiment. The enlarged side view 750 is shown by the dashed circle in cross-sectional side view 650 of FIG. 6B, this enlarged view 750 provides a more detailed view of the area around reaction vessel chamber 610.

The chassis portion 535 of the labyrinth seal 530 is shown, with chassis inner trough 725 being formed between chassis inner concentric ring 525 and chassis outer concentric ring 520. Chassis outer trough 730 is formed outside of chassis outer concentric ring 525. Chassis inner concentric ring 525 surrounds chamber opening 430. Alternatively, one can say that chassis inner trough 720 and chamber opening 430 form chassis inner concentric ring 525, and one can say that chassis outer trough 730 and chassis inner trough 725 form chassis outer concentric ring 520.

As previously discussed, the reaction vessel 105 can have a first portion 710 of a kinematic cylindrical joint 720 that is a fin 710 that fits within a second portion 740 of the kinematic cylindrical joint 720 that is a cylindrical feature of the reaction vessel chamber 610. The clearance groove 760 has above it the tapered portion 755 which can guide the collet 795 and/or the reaction vessel 105 into the reaction vessel chamber 610. Below the clearance groove 760 may be the tapered portion 765 to guide or further guide the reaction vessel 105 into the reaction vessel chamber 610. The chamber opening 430 above the tapered portion 755 provides external access to the reaction vessel chamber 610. When the reaction vessel 105 is seated within the reaction vessel chamber 610, the bottom (i.e., the nose 735) of the reaction vessel 105 engages with the first portion 745 and thereby forms the kinematic spherical joint 705.

The light from the light passage 640, after passing through the reaction vessel chamber 610 and reaction vessel 105, if present, enters the PMT 630 through aperture 635. Photons emitted from a sample in reaction vessel 105 also enter PMT 630 through aperture 635.

Figure 7C:
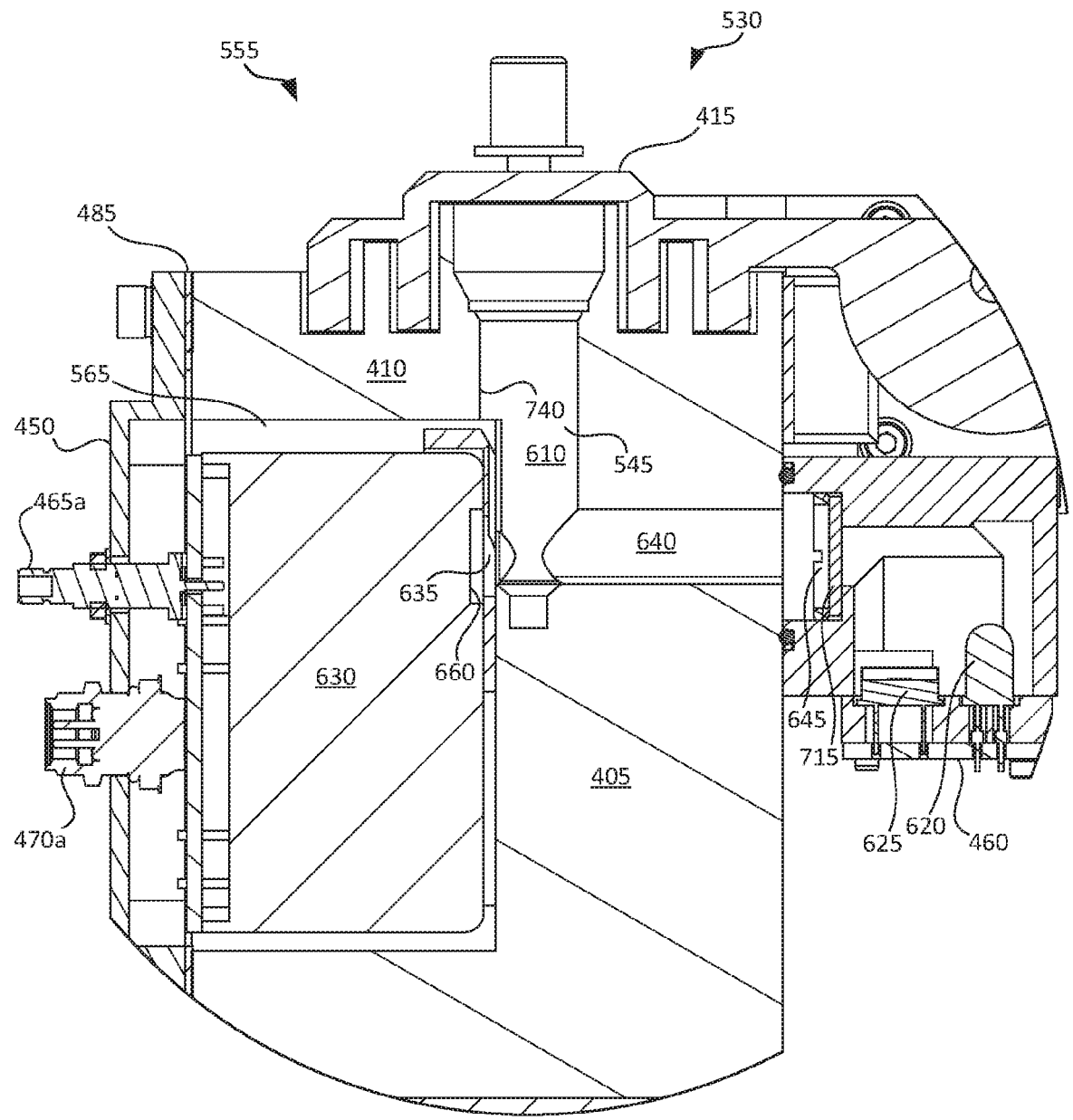
FIG. 7C is an enlarged partial cross-sectional side view with a cap closed, illustrating the example luminometer of FIG. 4, according to an embodiment.
Figure 7D:
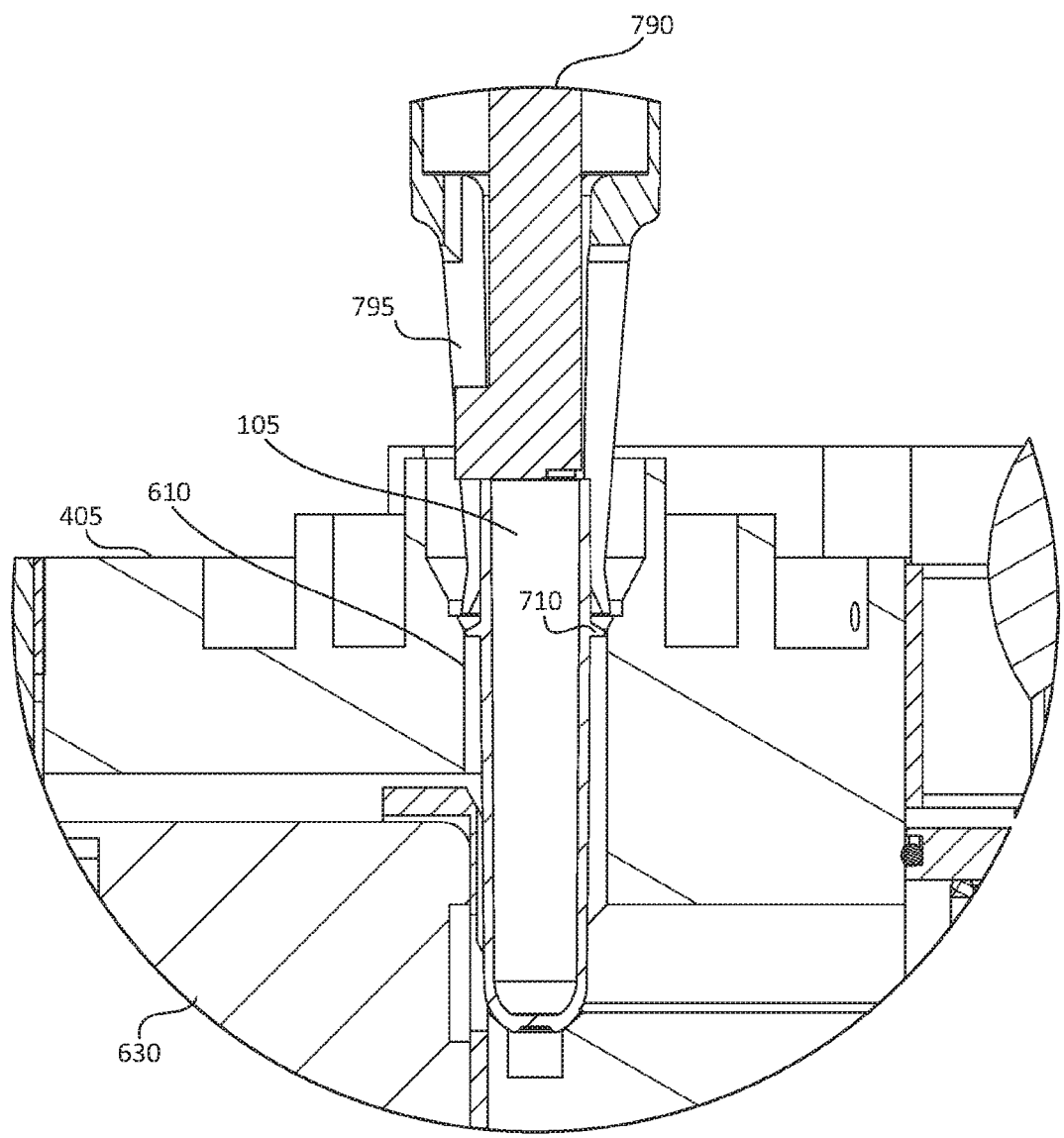
FIG. 7D is an enlarged partial cross-sectional side view with the cap of FIG. 7C opened, illustrating the example luminometer of FIG. 4 and a portion of a pick-and-place unit, according to an embodiment.

FIG. 7C illustrates an enlarged partial side view of the luminometer 400 with the cap 415 closed so that the luminometer 400 is in a closed configuration 555. The labyrinth seal 530 is engaged with the concentric rings 520, 525 of the chassis portion 535 of the labyrinth seal 530 intermeshed with the concentric rings 505, 510 of the cap portion 540 of the labyrinth seal 530.

Luminometer 400 may be used to perform assays. In use, cap 415 can be opened, which can trigger a sensor to send a signal to the luminometer computer system that can cause a shutter 660 to close to protect the PMT 630 from damage due to overexposure to light. A reaction vessel 105 can be positioned within the reaction vessel chamber 610. The reaction vessel 105 can contain a light emitting sample. When placed in the reaction vessel chamber 610, the spherical nose 735 of the reaction vessel 105 can secure the reaction vessel 105 via the kinematic spherical joint 705, and the fin 710 can secure the reaction vessel 105 via the kinematic cylindrical joint 720. (As the thickness of the fin 710 is small in relation to the outer diameter of the fin 710, the joint 720 primarily constrains a point at the center of the fin 710 to the axis 765 of the cylinder 740 of the reaction vessel chamber 610.) While no specimen is depicted in reaction vessel 105 within luminometer 400, a specimen or sample, such as the patient sample 165 as described with respect to FIG. 1 can be in the reaction vessel 105.

After the reaction vessel 105 is secured, the cap 415 can close to engage the cap portion 540 of the labyrinth seal 530 with the chassis portion 535 of the labyrinth seal 530 to form a dark chamber 545 (i.e., to exclude external light from the reaction vessel chamber 610 and from the light passage 640). Once the cap 415 is closed, the sensor can send a signal to the luminometer computer system (e.g., the luminometer controller 905) that can cause the shutter 660 to open, exposing the aperture 635 and thereby PMT 630 to the light passage 640 and/or the reaction vessel chamber 610. The PMT 630 can detect the photons emitting from the sample in the reaction vessel 105 through the aperture 635. The photon emission can be processed by the luminometer 400 as described in more detail with respect to FIGS. 9A-14.

After a threshold period of time, for example 1 second, the assay reading can be completed by the PMT 630. Multiple assay reads may be performed on the same sample sequentially. A median value of the reads may be reported as the result. The cap 415 can open, the reaction vessel 105 can be removed from the reaction vessel chamber 610 (e.g., by the collet 795 of the pick-and-place unit 790), and the cap 415 can close. Once closed with no reaction vessel 105 in the reaction vessel chamber 610, test cycle calibration can be run using the calibration unit 460. Referring to FIG. 6A, the LED 620 can emit a known photon or light power value based on an input voltage to the LED 620. The photodiode 625 can measure the photon emission to confirm the LED 620 is functioning properly and/or to provide feedback control. For example, the photodiode 625 can send a signal indicating the LED output value to the luminometer computer system (e.g., the luminometer controller 905), which can confirm the value. Output of the photodiode 625 may be used as feedback to control the output of the LED 620. The light from the LED 620 can shine off of the interior of the calibration unit housing (which can be, for example, anodized aluminum), and emit from the calibration unit 460 through calibration unit aperture 645. Referring back to FIG. 7A, filter 715 can filter the light emission from LED 620, and the filtered light can travel through light passage 640 to aperture 635. With no reaction vessel 105 present, the light can also travel up the reaction vessel chamber 610. The light that reaches aperture 635 can be measured by PMT 630. The measured light can be processed to calibrate the PMT 630 as described in further detail herein. The processes of performing an assay 100 and test cycle calibration can repeat. Optionally, the test cycle calibration can be executed between each assay. Optionally, the test cycle calibration can be executed less frequently.

Figure 8:
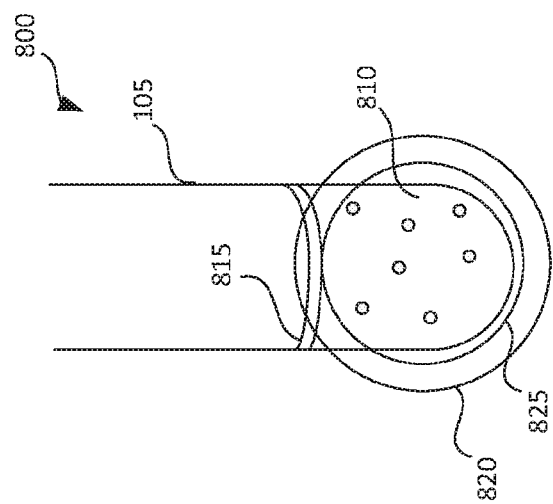
FIG. 8 is a schematic diagram that illustrates an example aperture view of the luminometer of FIG. 4, according to an embodiment.

FIG. 8 illustrates an example aperture view 800 of a luminometer, according to an embodiment. As discussed with respect to FIG. 7A, the aperture 635 can be sized sufficiently to mitigate the inaccuracies of measuring a sample that includes a meniscus. FIG. 8 illustrates a portion of a reaction vessel 105 containing a sample 810 with a meniscus 815. The unshielded view 820 is exposed to the inaccuracies associated with the meniscus 815. A meniscus 815 can have bubbles and/or other unevenness that can cause the photon measurement within the luminometer 400 to be inaccurate. The shielded aperture view 825 can obtain a more accurate reading because it is shielded from the meniscus 815. The shielded aperture view 825 may be further reduced in size to wholly view only a portion of the reaction vessel 105 containing the sample 810. In some embodiments, shielded aperture view 825 can be implemented via a bracket 665 used to couple the PMT 630 to the chassis 405. The shielded aperture view 825 can be shielded by the bracket 665 (i.e., a light detector bracket) that couples the PMT 630 to the chassis 405. The bracket 665 can form a portion or a whole of the aperture 635 to create the shielded aperture view 825.

Figure 9A:
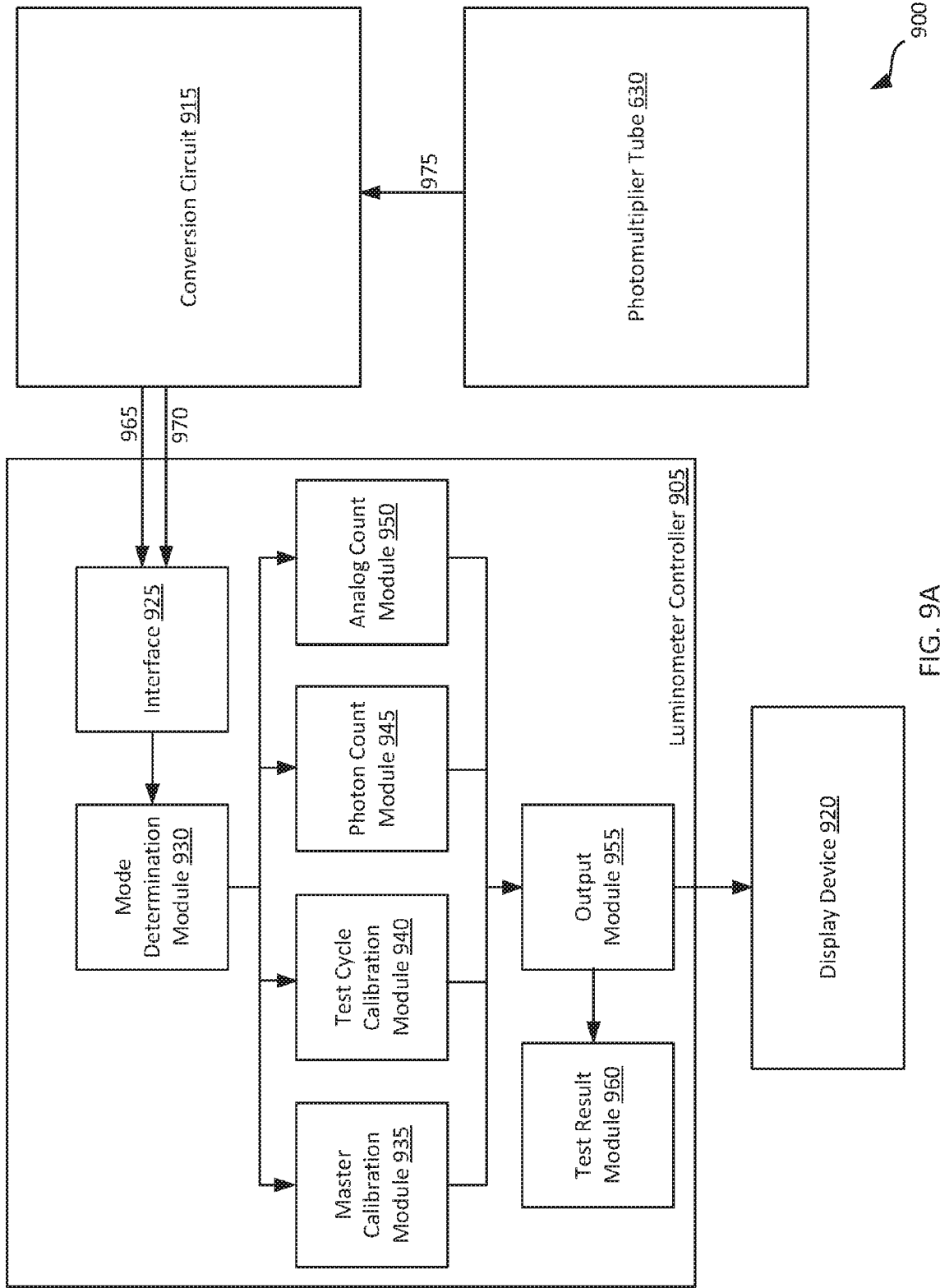
FIG. 9A is a simplified block diagram that illustrates components of the luminometer of FIG. 4, according to an embodiment.

FIG. 9A illustrates a simplified block diagram of a luminometer electrical system 900, according to an embodiment. The luminometer electrical system 900 can include the PMT 630, a conversion circuit 915, a luminometer controller 905, and a display device 920. While specific components and modules are depicted, functionality of one or more modules can be incorporated into a single module. Similarly, functionality of a single module can be spread amongst multiple modules without affecting the scope of this disclosure. Luminometer controller 905 may include additional modules and/or functionality than described below or depicted in FIG. 9A. For example, luminometer controller 905 may receive signals from sensors on luminometer 400 that luminometer controller 905 processes and that may cause other actions. As an example, luminometer controller 905 may receive a signal from a sensor indicating that the cap 415 is entering an open configuration. Luminometer controller 905 may, in response, send a signal to shutter 660 to close so that external light cannot enter PMT 630 to avoid damaging PMT 630.

The PMT 630 can receive a light emission through an aperture, such as luminometer aperture 635. The aperture 635 can render shielded aperture view 825. The PMT 630 outputs PMT output signal 975 based on the received light emission. The PMT output signal 975 can include two components including analog current. The PMT output signal 975 can be received by the conversion circuit 915. The conversion circuit 915 is shown in more detail in FIG. 9B.

Figure 9B:
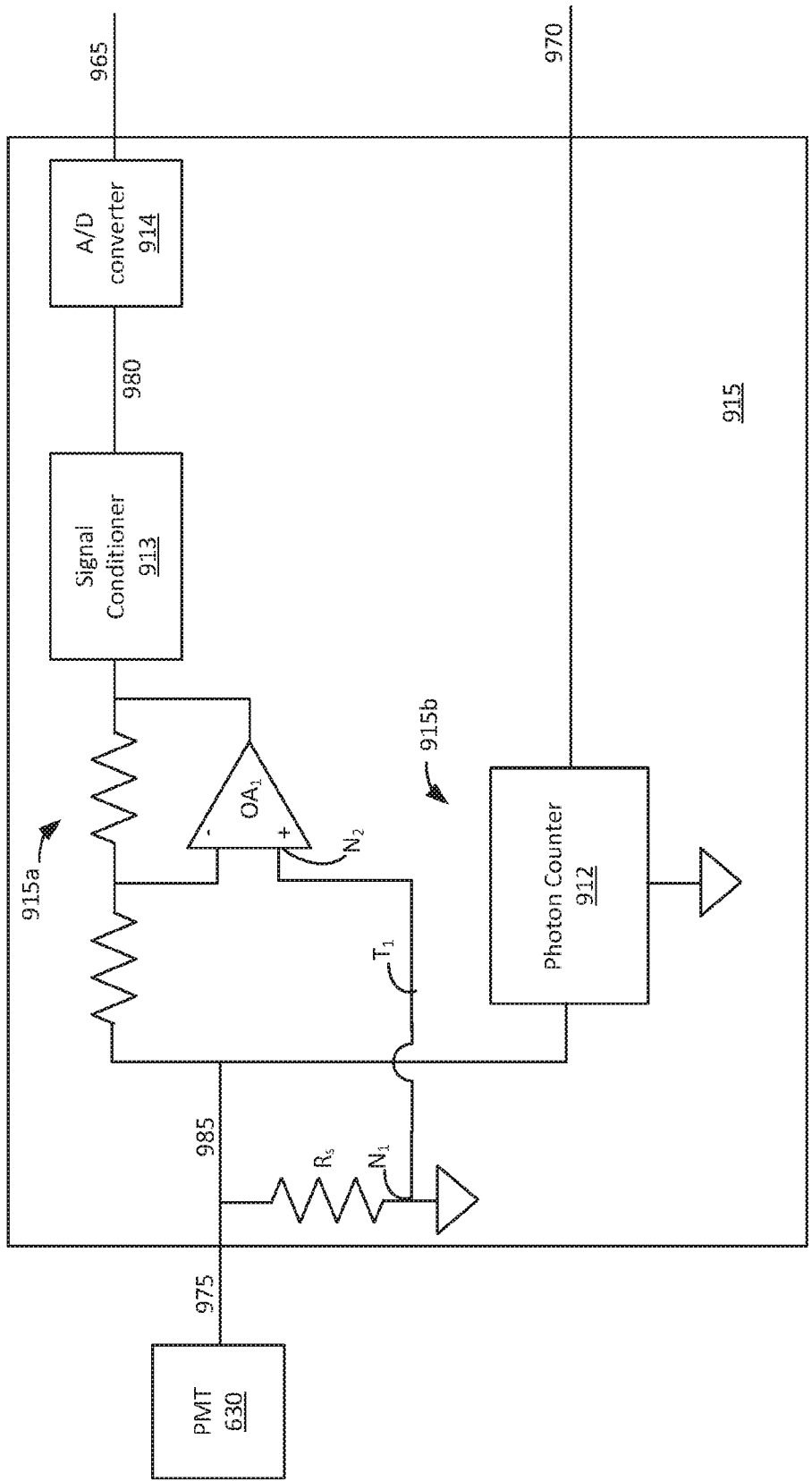
FIG. 9B is a simplified circuit diagram of a conversion circuit, according to an embodiment.

FIG. 9B illustrates the conversion circuit 915, which includes front end circuitry. The front end circuitry may include sense resistor $R_S$, that converts analog current in PMT output signal 975 into analog voltage 985. The conversion circuit 915 may be configured to receive and collect the PMT output signal 975 in increments over a period of time. For example, the PMT output signal 975 may be collected in 20 millisecond increments for a second to collect 50 increments. The values collected in each increment may then be averaged to generate a single value. The conversion circuit 915 includes an analog circuit portion 915a and a photon counter portion 915b. The analog circuit portion 915a is configured to convert the analog voltage 985 into an assay analog voltage 980 (i.e., an analog voltage). In other embodiments, an analog circuit portion is configured to transfer the analog current from PMT output signal 975 as an assay analog current (i.e., an analog current). Such an analog voltage and such an analog current may be collectively referred to as an analog signal. The analog circuit portion 915a includes a first stage amplifier. $OA_1$ (e.g., an operational amplifier, op-amp, etc.) and may include signal conditioner 913 including, for example, additional amplifiers and/or signal filters. The assay analog voltage 980 is digitized by analog to digital (A/D) converter 914 and the digitized assay analog voltage 965 is transmitted to the interface 925 of luminometer controller 905. The analog circuit portion 915a includes a dedicated electrical connection $T_1$ between a terminal $N_1$ of the current sensing resistor $R_S$ and a terminal $N_2$ of the first stage amplifier $OA_1$. If the analog circuit portion 915a is disposed on a printed circuit board, the terminal $N_1$ of the current sensing resistor $R_S$ and/or the terminal $N_2$ of the first stage amplifier $OA_1$ may also be connected to the ground plane of the conversion circuit 915. The dedicated electrical connection $T_1$, being connected directly between the resistor terminal $N_1$ and the amplifier terminal $N_2$, carries the return signal for the analog voltage 985, and does not substantially carry other signals which may be present on the ground plane. The presence of signals other than the return signal between the terminals $N_1$. $N_2$ of the resistor $R_S$ and the first stage amplifier $OA_1$ reduces the signal to noise ratio at the first stage amplifier terminal $N_2$. The use of the dedicated electrical connection $T_1$ can provide a signal to noise ratio between approximately 10 to 1,000,000, for example, approximately 100. In certain embodiments, the use of the dedicated electrical connection $T_1$ can provide a signal to noise ratio between approximately 500 to 4,000. For example, in some scenarios, the use of the dedicated electrical connection $T_1$ can increase the signal to noise ratio at the terminal $N_2$ of the first stage amplifier $OA_1$ by at least a factor of approximately 10 or even a factor of approximately 100 when compared to an identical circuit that does not include the dedicated electrical connection. As shown in FIG. 9B, the conversion circuit 915 further includes a photon counter portion 915b comprising a photon counter 912 that counts analog voltage pulses of the analog voltage 985 and provides a digitized assay photon count 970 to the interface 925 of the luminometer controller 905.

Figure 15:
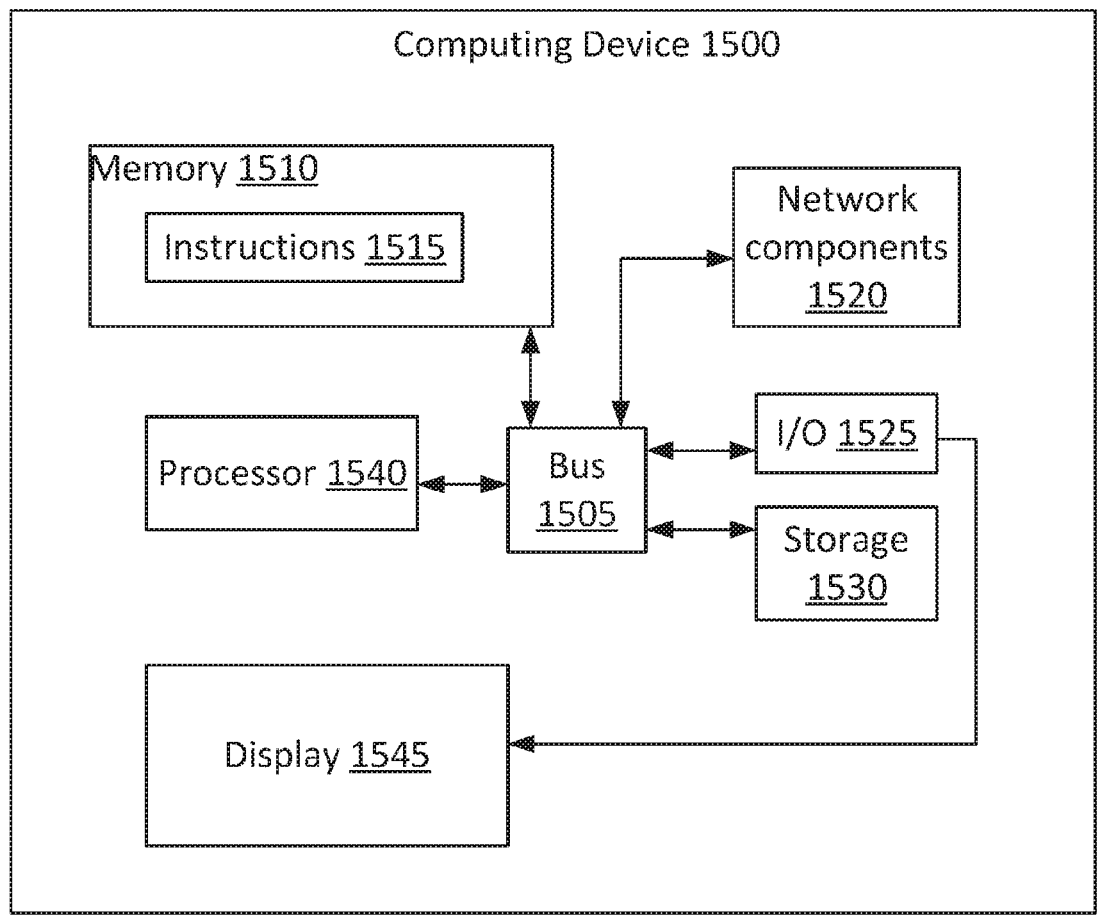
FIG. 15 is a schematic diagram that illustrates an example computer system, according to an embodiment.

Returning to FIG. 9A, luminometer controller 905 can be any suitable computer system, such as computer system 1500 as described with respect to FIG. 15. Luminometer controller 905 can include the interface 925, a mode determination module 930, a master calibration module 935, a test cycle calibration module 940, a photon count module 945, an analog count module 950, an output module 955, and a test result module 960.

The mode determination module 930 can determine the mode of the PMT 630. A master calibration mode can be executed to calibrate the PMT 630 upon initial build. In some embodiments, the master calibration mode can be executed at other times including on a periodic basis, such as monthly. Alternatively, the master calibration mode can be executed upon determination that the PMT 630 has drifted too far from initial calibration. A test calibration mode can be executed to calibrate the PMT 630 between test cycles that perform an assay. Optionally, the test calibration mode can be executed between each test cycle. Optionally, the calibration mode can be executed periodically, such as every 10 minutes, for example or after every $10^{th}$ test cycle as another example. An assay mode can be executed to calculate an assay result. This is also called a test cycle.

Figure 10A:
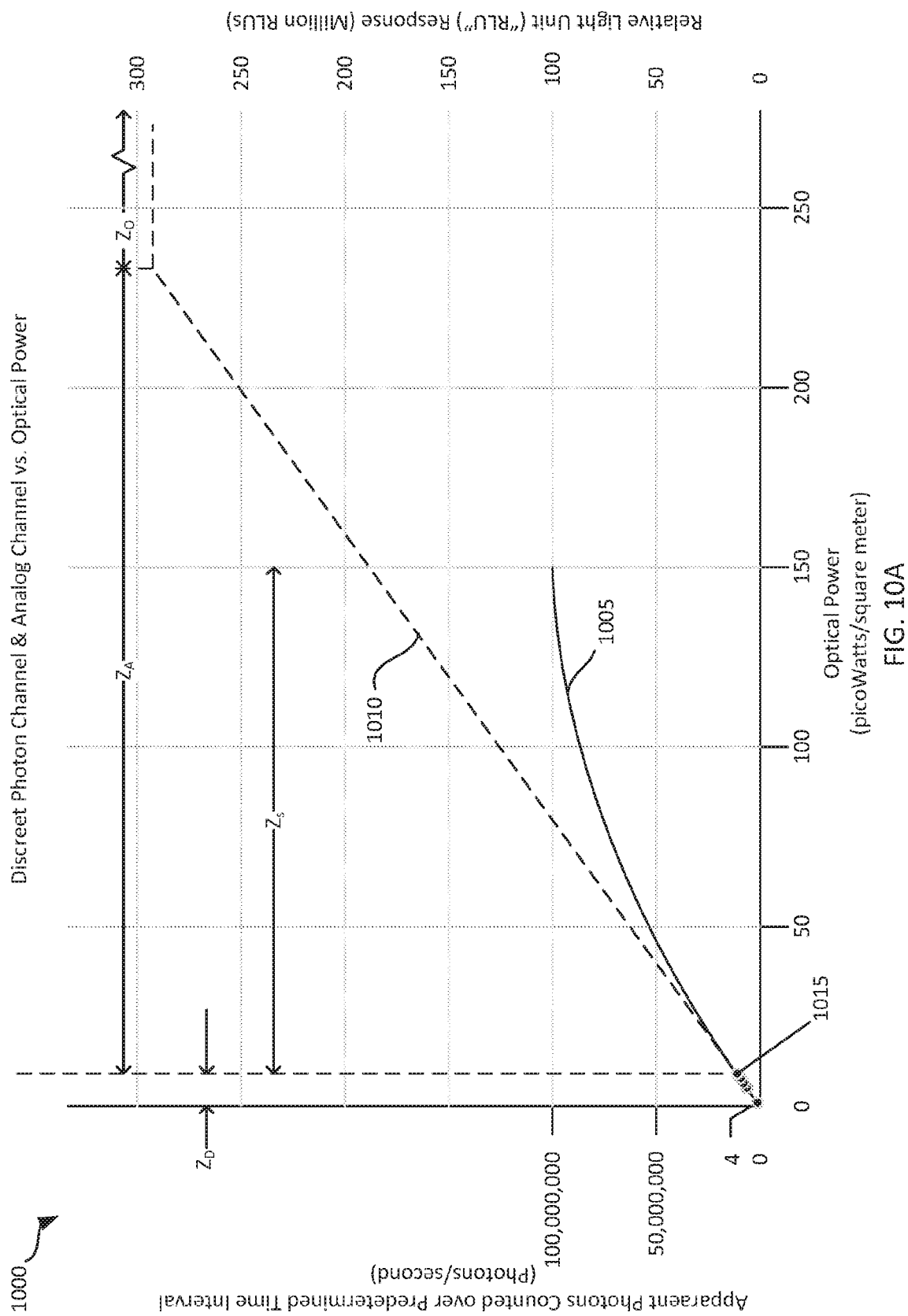
FIG. 10A is an example graph of the luminometer output response in relation to optical power input, according to an embodiment.
Figure 10B:
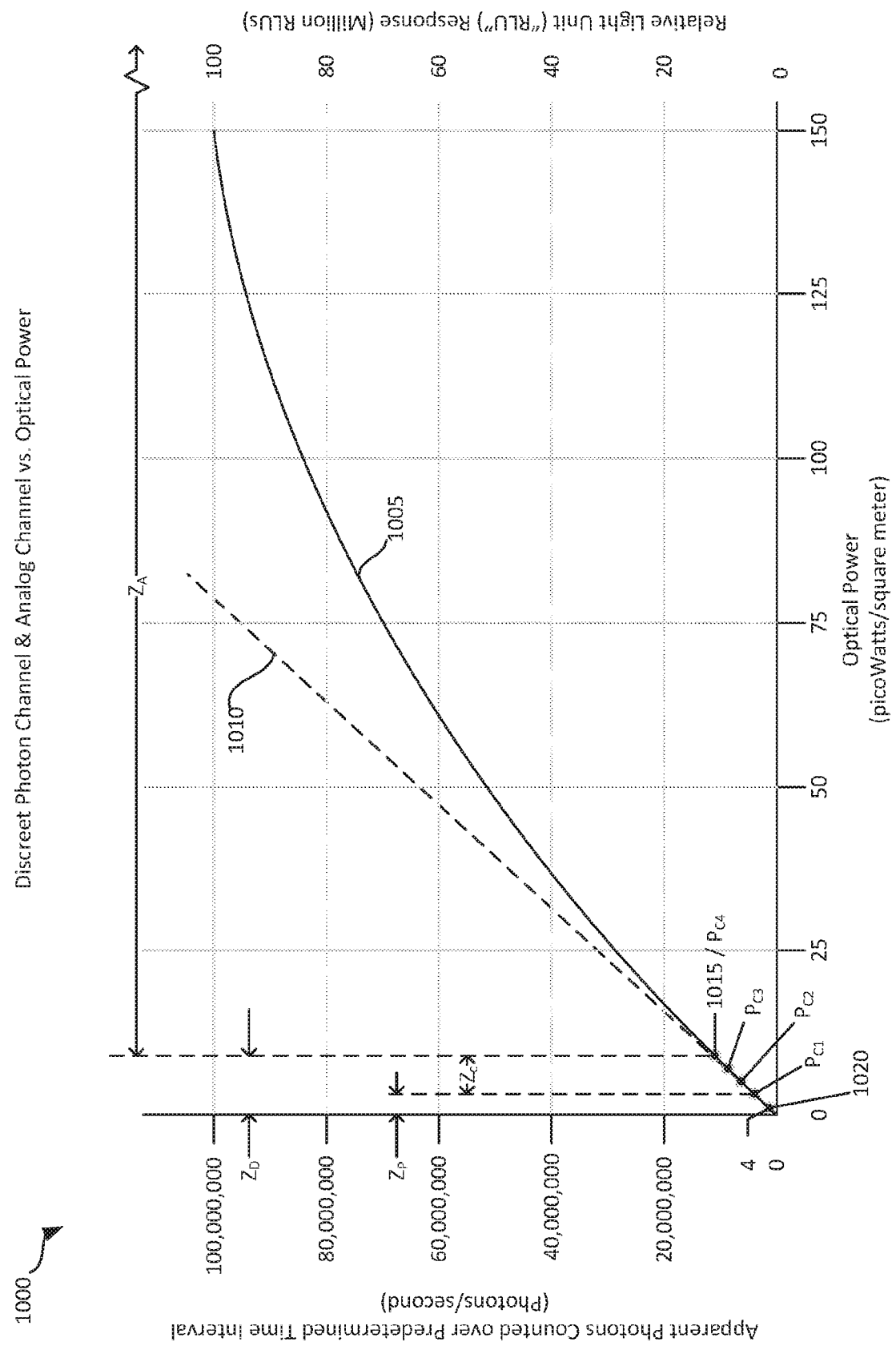
FIG. 10B is an enlarged portion of the example graph of FIG. 10A.

The master calibration module 935 can be used when the PMT 630 is in master calibration mode. The gain of PMT 630 can be set to operate in a plateau region, as is known in the art of PMTs. The PMT gain can be set by exposing the PMT 630 to a calibrated light source with a known RLU output response. For example a NIST (National Institute of Standards and Technology) approved and traceable calibrated light source may be used. The calibrated light source may be an external light source that is put in the dark chamber 545 formed by closing the cap 415 of the luminometer 400. Alternatively, the calibrated light source may include an external light source and a light source portion of a labyrinth seal, similar to the cap portion 540 of the labyrinth seal 530, that similarly forms the dark chamber 545 with the light source portion of the labyrinth seal in lieu of the cap portion 540 of the labyrinth seal 530 (and with the cap 415 of the luminometer 400 open). Alternatively, the PMT may be removed from the chassis 405 and temporarily replaced with a NIST (National Institute of Standards and Technology) approved and traceable calibrated light sensor. The NIST light sensor may be used to calibrate the LED 620. The gain of the PMT 630 may be adjusted until the RLU output response of the PMT 630 corresponds to the calibrated light source. For example, the expected RLU output response to the calibrated light source may be 10 million RLUs, so the gain of the PMT 630 may be adjusted until the luminometer 400 provides an RLU output response of 10 million RLUs. Once the PMT gain is set, the master calibration module can calculate the discreet/analog crossover 1015 (as depicted in FIGS. 10A and 10B) of the PMT 630. The discreet/analog crossover 1015 may be represented as an RLU value. The discreet/analog crossover 1015, once identified, can be a predetermined value used to identify whether a linear function or an apparent photon count should be relied upon for generating an output of the luminometer 400. The relationship between the digitized assay analog voltage 965 and the digitized assay photon count 970 is used to derive a linear function 1010, as described in detail below. The discreet/analog crossover 1015 can be calculated using the PMT gain previously set. The PMT gain is set to a percentage of a maximum gain for that PMT 630. For example, the gain of the PMT 630 may have been set to eight-five percent of the maximum PMT gain. Further, a known ideal discreet/analog crossover value can be used, for example, a known ideal discreet analog crossover value can be twelve million five hundred thousand RLUs. The ideal discreet/analog crossover value may be determined based on the circuitry of the luminometer 400. The known ideal discreet/analog crossover value and the PMT gain are used to calculate the discreet/analog crossover 1015 for PMT 630. The percentage of the PMT gain multiplied by the known ideal discreet/analog crossover value determines the discreet/analog crossover 1015. For example, eighty-five percent of twelve million five hundred thousand RLUs is ten million six hundred and twenty-five thousand RLUs, which is the discreet/analog crossover 1015 in this example. The discreet/analog crossover 1015 represents the RLU output response value used to determine whether the digitized assay analog voltage 965 is used to calculate the RLU output response (if the digitized assay photon count 970 is above the discreet/analog crossover 1015) or if the digitized assay photon count 970 is used is reported as the RLU output response (if the digitized assay photon count 970 is below the discreet/analog crossover 1015). As discussed with respect to FIGS. 2A-2G, as the light input (optical power) increases, the photon count becomes saturated due to the overlapping signal pulses. Accordingly, PMT 630 has a crossover point at which the light input is too high to read discrete photon counts accurately. The discreet/analog crossover 1015 is used to ensure that the RLU output response is accurately reported by ensuring that the discreet photon count is not used above the discreet/analog crossover 1015.

Once the discreet/analog crossover 1015 is calculated, the master calibration module 935 can calibrate the LED 620 of calibration unit 460 (i.e., internal calibration light source). The external calibration light source is removed from the system. A high calibration input voltage for the LED 620 can be identified by increasing the voltage applied to the LED 620 until the RLU output response of the PMT 630 is at the discreet/analog crossover 1015. Using the above example, the voltage applied to the LED is increased until the RLU output response of the PMT 630 is ten million six hundred and twenty-five thousand RLUs. The high calibration input voltage value can be saved for later use in a memory of the luminometer computer system (e.g. the luminometer controller 905). The lowest calibration point $P_{C1}$ (shown in FIG. 10B) can be identified by determining a low calibration input voltage to apply to the LED 620 such that the analog output response of the PMT 630 is discernable (measurable). As described in FIG. 10B, the PMT 630 does not register an analog component 965 at very low light levels, which is depicted in FIG. 10B as the discreet photon count only zone $Z_P$. The low calibration input voltage is identified by lowering the voltage applied to the LED 620 to zero volts. The voltage can be increased slowly until an analog output response 965 is detected from the PMT 630. Optionally, an additional buffer voltage (e.g., ten percent) can be applied to the low calibration input voltage to ensure that the voltage applied to the LED 620 will result in an analog output response 965 of the PMT 630. The RLU output response of the PMT 630 when the low calibration input voltage is applied to the LED 620 is depicted in FIG. 10B as $P_{C1}$. The low % calibration input voltage and the associated RLU output response can be saved in a memory of the luminometer computer system 905.

The master calibration module 935 can generate a linear function representing curve 1010 as shown in FIGS. 10A and 10B. Curve 1010 represents the linear output response of the PMT 630 at any given optical power (lower than an overrange zone $Z_O$). The linear function can be calculated by first identifying additional calibration points (e.g., $P_{C2}$ and $P_{C3}$) within a calibration zone $Z_C$. The voltages between the low calibration input voltage and the high calibration input voltage can be divided into, for example, three segments. The number of segments can be more or fewer than three, and the segments can optionally be equally spaced. In the example of three equal segments, the high calibration input voltage and the low calibration input voltage can be used as the voltages at the outer bounds of calibration zone $Z_C$, outside points $P_{C1}$ and $P_{C4}$, and two additional voltage values, $P_{C2}$ and $P_{C3}$, can be obtained to designate the three equal segments. As an example, if the low calibration input voltage value is two volts and the high calibration input voltage value is eight volts, the two intermediate voltage values are four volts and six volts to get three equal segments. The four calibration input voltage values can each be applied to the LED 620 to generate four associated RLU output responses from the PMT 630. The four RLU output responses can be used in a linear regression to obtain the linear function slope and offset of linear curve 1010. The offset value will be an RLU value. The linear function (y=m*x+b), using the slope (m) and offset (b), identified using the linear regression, is stored in the memory of the luminometer computer system 905. When graphed, the linear equation is represented by curve 1010. Stated differently, alight source 620 measured by PMT 630 adjusted through the range of optical power from zero to the upper portion of the analog measurement zone $Z_A$ will generate the PMT output response curve 1010. Alternatively, a light source 620 measured by PMT 630 adjusted through the range of optical power from the lower portion of the calibration zone $Z_C$ to the upper portion of the analog measurement zone $Z_A$ will generate the PMT output response curve 1010.

FIG. 10A illustrates graph 1000 depicting the analog and discreet RLU output response of PMT 630 in relation to the optical power of the input, according to an embodiment. The curve 1005 represents the apparent photon count 970 as counted by the photon counter 912. As the optical power increases, the RLU output response, depicted by curve 1005, becomes inaccurate because the photon count saturates such that individual photons increasingly cannot be counted. The curve 1010 represents the RLU output response of PMT 630 based on the digitized assay analog voltage 965 at optical powers resulting in an RLU output response greater than the discreet/analog crossover 1015 and based on the digitized apparent assay photon count 970 at optical powers at or below the discreet/analog crossover 1015. Curve 1010 further represents the line extrapolated by master calibration module 935 of FIG. 9A. Because of signal saturation, when the prior luminometer systems and methods are used to calculate the RLU output of a PMT, the non-linear curve 1005 is generated. As depicted in the graph 1000, the linearly of the RLU output response decreases as the optical power increases when using curve 1005. However, testing with known values shows that the digitized assay analog voltage 965 is accurate for determining the RLU output response of the luminometer 400 at optical powers beyond those that result in the non-linear RLU output response depicted by curve 1005 of FIGS. 10A and 10B and/or curve 305 of FIG. 3.

Graph 1000 can be used to show the various zones of operability of the luminometer 400. As shown in FIG. 10A, within analog measurement zone $Z_A$, an analog measurement 965 from the conversion circuit 915 can be used to determine the RLU output response of the luminometer 400. The analog measurement zone $Z_A$ has a lower bound at the discreet/analog crossover 1015. The discreet/analog crossover 1015 is approximately at the optical power value (i.e., light power value) of nine picoWatts per square meter in this example and results in an RLU response of approximately eleven million RLUs. The upper bound of the analog measurement zone $Z_A$ is approximately at optical input of two hundred and forty picoWatts per square meter and approximately an RLU output response of the luminometer 400 of approximately two hundred and ninety-five million RLUs. Curve 1010 indicates the accurate and linear RLU output response within the analog measurement zone $Z_A$. As indicated by curve 1005, the RLU output response based on the digitized apparent assay photon count 970 becomes non-linear within the analog measurement zone $Z_A$.

The overrange zone $Z_O$ falls beyond the analog measurement zone $Z_A$. The overrange zone $Z_O$ is approximately when the optical power exceeds approximately two hundred and forty picoWatts per square meter in this example. In overrange zone $Z_O$, the circuit board and firmware are limiting. Within overrange zone $Z_O$, the optical power exceeds the ability of the luminometer 400 to measure and output a valid RLU output response.

As discussed above, the linear portion of the digitized apparent assay photon count 970 provides an accurate measurement of photons. The discreet photon count measurement zone $Z_D$ is the zone within which the photon counter portion 915b can identify discreet photons striking the photocathode of the PMT 630 and output the photon count. Discreet photon count measurement zone $Z_D$ is within optical power of zero and approximately nine picoWatts per square meter, in this example. The upper bound of the discreet photon count measurement zone $Z_D$ is the discreet/analog crossover 1015. The lower threshold of the discreet photon count measurement zone $Z_D$ is zero. The RLU output response within the discreet photon count measurement zone $Z_D$ is approximately between zero RLU and eleven million RLU. Within the discreet photon count measurement zone $Z_D$, the indicated RLU output response based on the apparent digitized assay photon count 970 is linear.

The photon count of the photon counter portion 915b begins saturating in the saturation zone $Z_S$, when optical power exceeds the discreet photon count measurement zone $Z_D$. Within the saturation zone $Z_S$, indicated output from the photon counter 912 of the photon counter portion 915b as the digitized apparent assay photon count 970 is a lower RLU value than the actual RLU value, as indicated by curve 1005. However, within the saturation zone $Z_S$, the curve 1010 representing the RLU output response based on the digitized assay analog voltage 965 is accurate and linear. Within the saturation zone $Z_S$, the linear function generated from the master calibration module 935 is used to obtain the RLU output response based on the digitized assay analog voltage 965.

FIG. 10B illustrates an enlarged partial view of graph 1000. As shown in FIG. 10B, the RLU output response based on the digitized apparent assay photon count (shown by curve 1005) indicates that pulse pair resolution becomes significant at approximately the discreet/analog crossover 1015. Further, the pulse pair resolution results in saturation at approximately an RLU output response of one hundred million photons per second. Calibration point $P_{C1}$, calibration point $P_{C2}$, calibration point $P_{C3}$, and calibration point $P_{C4}$ (e.g., at discreet/analog crossover 1015) are illustrated, and are shown within the discreet photon count measurement zone $Z_D$ and within the calibration zone $Z_C$. The uppermost calibration point $P_{C4}$ is illustrated as the discreet/analog crossover 1015 value. The lowest calibration point $P_{C1}$ is illustrated as the lowest value from which an analog output response can be discerned from the PMT 630 by the analog circuit portion 915a. At optical powers below the lowest calibration point $P_{C1}$ is the photon counting only zone $Z_P$. Within the photon counting only zone $Z_P$, the conversion circuit 915 of the luminometer 400 outputs a photon count 970 only (i.e., no analog output 965 is discernable) and photon counting for RLU output response is the digitized assay photon count 970 from the conversion circuit 915. Example discreet point 1020 within photon counting only zone $Z_P$ has an RLU output response value of 4 RLU, which is the apparent photon value counted per second. At this optical power, no analog current component is detectable in the PMT output signal 975. As illustrated, the calibration zone $Z_C$ has an upper bound of the discreet/analog crossover 1015 and a lower bound at the lowest calibration point $P_{C1}$. Within the calibration zone $Z_C$, the digitized apparent assay photon count 970 is used to report the RLU output response of the luminometer 400. At optical powers above the calibration zone $Z_C$ (i.e., in the analog measurement zone $Z_A$ but not the overrange zone $Z_O$), the digitized assay analog voltage 970 is used to determine the RLU output response of the luminometer 400. Within the calibration zone $Z_C$, calibration point $P_{C1}$, calibration point $P_{C2}$, calibration point $P_{C3}$, and calibration point $P_{C4}$ are obtained to generate the linear function 1010 for use in the analog measurement zone $Z_A$.

Returning to FIG. 9A, test cycle calibration module 940 can execute a test cycle calibration when the mode determination module 930 determines that the luminometer 400 is in test cycle calibration mode. The test cycle calibration module 940 can be used to correct for noise and/or drift. The calibration can re-linearize the luminometer 400 by recalculating the linear function. This type of re-linearization may be performed, for example, once each month. The re-linearization can include adjusting the gain of the PMT 630 until the RLU output response is the discreet/analog crossover 1015 when the high calibration input voltage is applied to LED 620. This PMT gain adjustment may help resolve drift of the PMT 630 and/or account for noise within the system. After the PMT gain is adjusted, the low calibration input voltage is applied to the LED 620 and the associate RLU output response is saved. The two additional calibration input voltages previously determined by the master calibration module 935 can be applied to the LED 620 and the associated RLU output response can be obtained at each calibration input voltage. The linear regression can be applied to the RLU output response values to obtain the new slope (m) and offset (b) for the linear function. The new linear function can then replace the old linear function (obtained from the master calibration module 935) and be stored for use when performing assays.

Mode determination module 930 can determine when an assay is being performed. If in assay test mode, the mode determination module 930 can determine whether the digitized assay photon count 970 is above the discreet/analog crossover 1015. If the digitized assay photon count 970 is above the discreet/analog crossover 1015, the mode determination module 930 can instruct the analog count module 950 to determine the RLU output response of the luminometer 400 using the digitized assay analog voltage 965. If the digitized assay photon count 970 does not exceed the discreet/analog crossover 1015, the mode determination module 930 can instruct the photon count module 945 to determine the RLU output response of the luminometer 400 using the digitized assay photon count 970.

The photon count module 945 can determine the RLU output response using the digitized assay photon count 970 by, for example, reporting the digitized assay photon count 970.

The analog count module 950 can determine the RLU output response by entering the digitized assay analog voltage 965 into the linear function that is saved and was generated by the master calibration module 935 or updated by the test cycle calibration module 940. The digitized assay analog voltage 965 can be used as the "x" variable (independent variable) of the linear function. The slope (m) and offset (b) can be used in the formula RLU output response=y=m*x+b. The analog count module 950 can report the RLU output response (i.e., "y" from y=m*x+b).

Each of the master calibration module 935, test cycle calibration module 940, photon count module 945, and analog count module 950 can output information, such as an RLU output response for the light detected by PMT 630 to output module 955. Output module 955 can provide information to a display device 920 for a user to view. Optionally, output module 955 can provide the information to test result module 960 for inclusion in a report, for example, to be provided to the patient that provided the patient sample tested in the assay.

Figure 11:
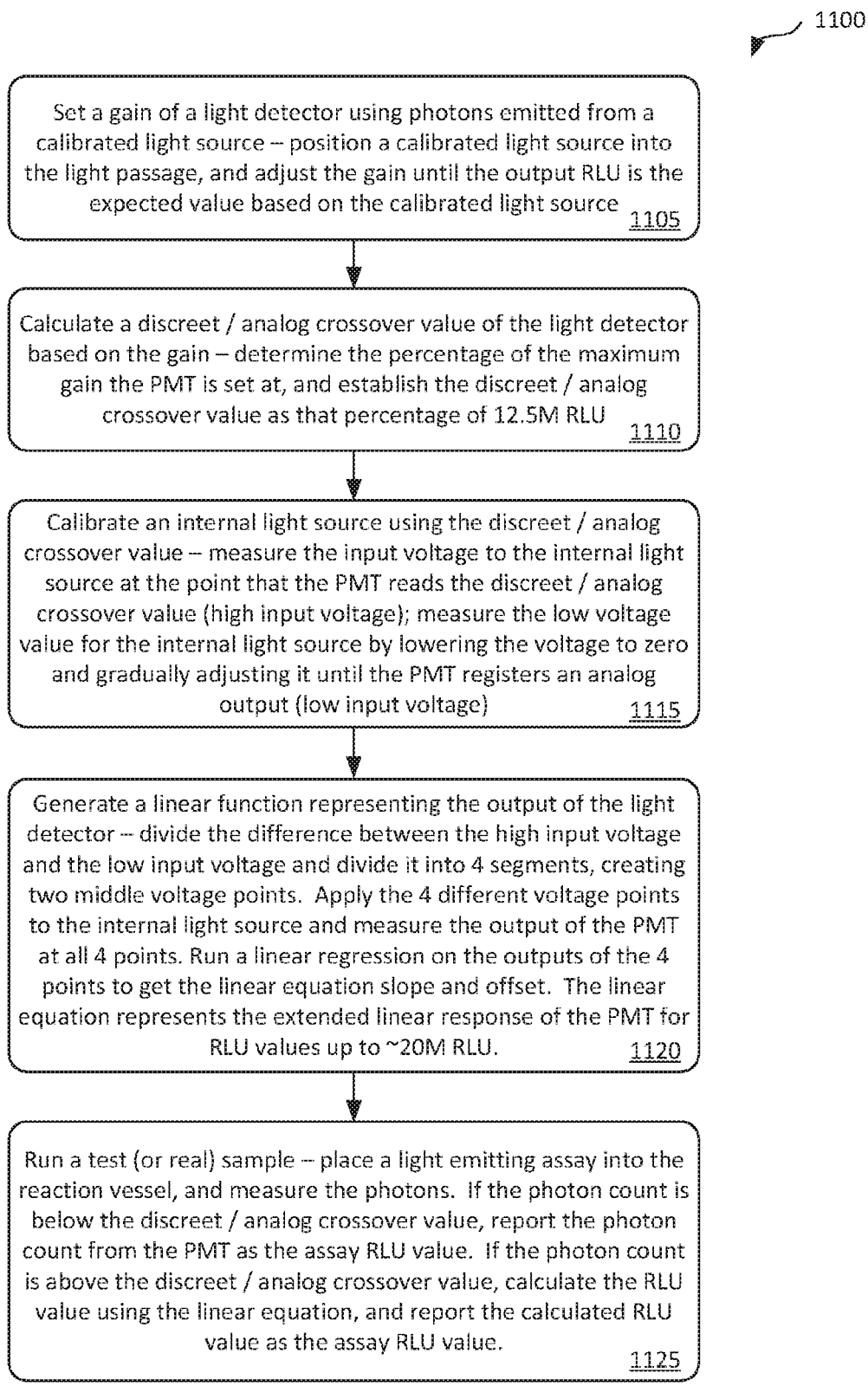
FIG. 11 is a flowchart depicting an example master calibration method of a luminometer, according to an embodiment.

FIG. 11 illustrates a master calibration method 1100 for extending signal linearity. The method 1100 can be performed by, for example, luminometer electrical system 900 of FIG. 9A, and more specifically by master calibration module 935. The method 1100 can begin with setting a gain of a light detector 630 using photons emitted from a calibrated light source at step 1105. As previously discussed, an external light source may be introduced into the reaction vessel chamber 610 of luminometer 400. The RLU output response for the calibrated light source may be known, and a gain of the PMT 630 can be adjusted until the known RLU output (expected output) response is received.

At step 1110 the master calibration module 935 can calculate the discreet/analog crossover value 1015 of the light detector (i.e., PMT 630) based on the gain. For example, the PMT gain may have been adjusted to a percentage of the maximum gain for the PMT 630. The percentage value can be used to identify the discreet/analog crossover value 1015 by taking the percentage of an ideal RLU output response. As an example, the ideal RLU output response may be twelve million five hundred thousand RLU. If the PMT gain is set to ninety percent of maximum, for example, the analog/discreet crossover 1015 is eleven million two hundred fifty thousand RLU.

At step 1115 the master calibration module 935 can calibrate the internal light source 620 using the discreet/analog crossover value 1015. Light source calibration method 1200 is described in FIG. 12.

Figure 12:
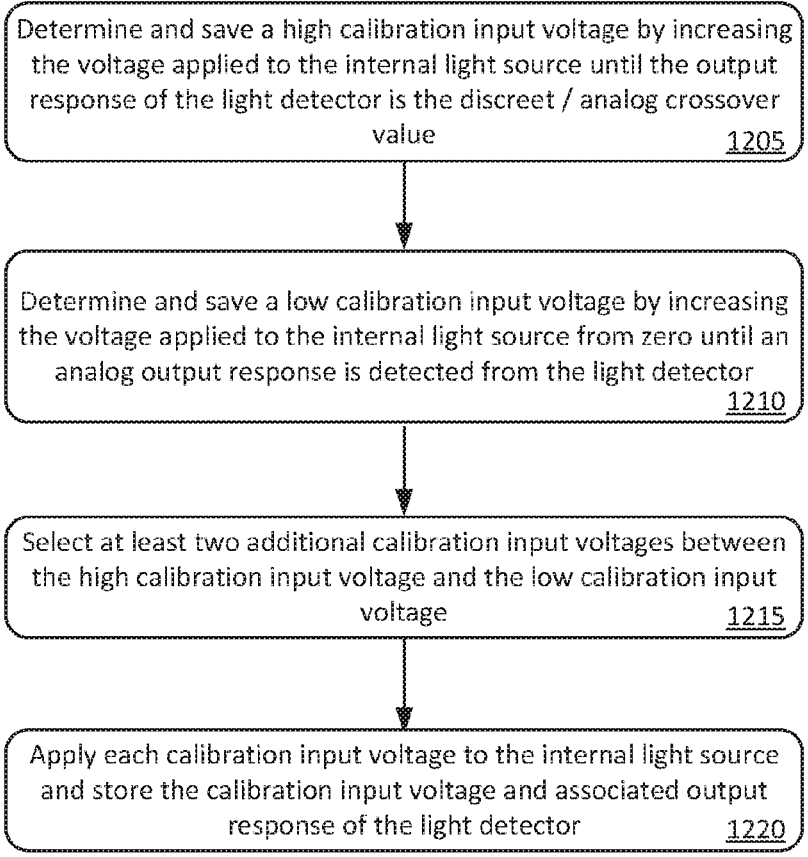
FIG. 12 is a flowchart depicting an example internal light source calibration method of a luminometer, according to an embodiment.

FIG. 12 illustrates alight source calibration method 1200, which provides additional detail of step 1115 of the master calibration method 1100. At step 1205 the master calibration module 935 can determine and save a high calibration input voltage. The high calibration input voltage is determined by increasing the voltage applied to the internal light source (i.e., LED 620) until the RLU output response of the luminometer 400 is the discreet/analog crossover value 1015.

At step 1210, the master calibration module 935 can determine and save the low calibration input voltage. The low calibration input voltage is determined by increasing the voltage applied to the internal light source 620 from zero volts until an analog output response is detected from the light detector (i.e. PMT 630). Below the low calibration input voltage, the RLU output response from the luminometer 400 is the digitized assay photon count 970 because there is no digitized assay analog voltage 965 detected.

At step 1215, the master calibration module 935 can select at least two additional calibration input voltages between the high calibration input voltage and the low calibration input voltage. For example, two equally distant input voltages can be calculated and used.

At step 1220, the master calibration module 935 can apply each calibration input voltage to the internal light source 620 and store the calibration input voltage and associated output response of the light detector 630. Using four calibration points will result in four associated RLU output response values. Any number greater than two calibration points can be used.

Returning to FIG. 11, at step 1120, the master calibration module 935 can apply a linear regression to the RLU output response values obtained from applying the calibration input values to the LED 620 to generate a linear function slope (m) and offset (b). The linear function represents the extended linear response of the PMT (light detector) for RLU values up to 20 million RLUs. Above 20 million RLUs, photoelectron pulses start to combine causing the curve 1005 to bend and thus become non-linear.

Figure 13:
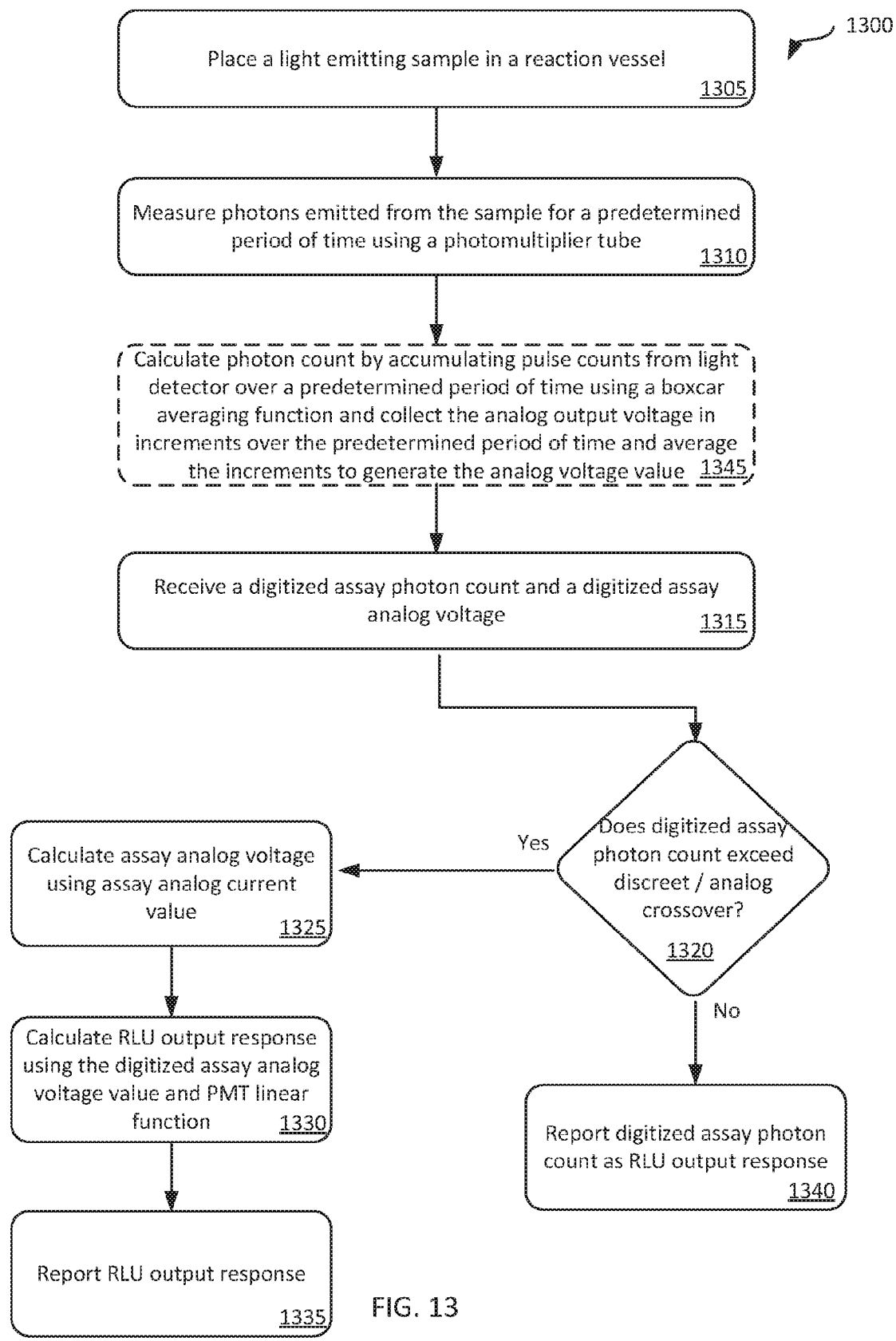
FIG. 13 is a flowchart depicting an example testing method with extended signal linearity of a luminometer, according to an embodiment.

At step 1125, a sample may be run. FIG. 13 illustrates a flowchart depicting a method 1300 for performing an assay 100 with luminometer 400. Method 1300 begins at step 1305 with placing a light emitting sample in a reaction vessel 105. A patient sample may first be placed in a reaction vessel 105, followed by various reagents and/or substrate materials. The light emitting sample may be generated through the process described in assay 100 with respect to FIG. 1 that results in the light emitting sample at stage 8. The reaction vessel (e.g., reaction vessel 105) can be placed in a reaction chamber (e.g., reaction vessel chamber 610). At step 1310, a PMT (e.g. PMT 630) can measure photons emitted from the processed sample for a predetermined period of time (e.g., 1 second). The output signal 975 from the PMT 630 can be captured incrementally over the period of time and averaged (using boxcar averaging) to generate a digitized apparent assay photon count 970 and a digitized assay analog voltage 965 by, for example, conversion circuit 915 as shown at optional step 1345. For example, the luminometer 400 may examine the light output of one processed sample every instrument pitch (e.g., 8 seconds). Within the instrument pitch, the luminometer 400 may perform three separate reads of the sample Each of the reads may be performed over a one second time period. The photon counter portion 915b thereby counts apparent photons from the processed sample three times while the processed sample is within the dark chamber 545 and derives a count for each of the three times. The reported digitized assay photon count 970 may be the middle (i.e., median) value of the three counts. By reporting the median value as the digitized assay photon count 970, outlier results, which may be caused by cosmic rays. X-rays, and/or other effects not from the sample, are rejected. The analog circuit portion 915a also collects one result over each of the three separate reads of the sample. In particular, during each one second sample read, 10,000 measurements of the voltage values 980 are averaged and reported as the digitized assay analog voltage 965 as shown at optional step 1345. However, only one of these three averaged values is used as the output further processed by the luminometer 400. For example, the averaged value that corresponds to the time period of the median value of the digitized assay photon count 970 may be used. The luminometer computer system (e.g., luminometer controller 905) can receive the digitized assay photon count 970 and digitized assay analog voltage 965 and determine, at step 1320, whether the digitized assay photon count 970 exceed the discreet/analog crossover 1015. If the digitized assay photon count 970 exceeds the discreet analog crossover 1015, the method 1300 continues at step 1325 to calculate the assay analog voltage 965 using the assay analog current value. Optionally, the assay analog voltage 965 can be calculated before determining whether the digitized assay photon count 970 exceeds the discreet/analog crossover 1015. At step 1330 the luminometer controller 905 can calculate the RLU output response using the digitized assay analog voltage 965 and the linear function. At step 1335, the luminometer controller 905 can report the RLU output response. If the digitized assay photon count 970 did not exceed the discreet/analog crossover 1015 at step 1320, the luminometer controller 905 can report the digitized apparent assay photon count 970 as the RLU output response at step 1340.

Figure 14:
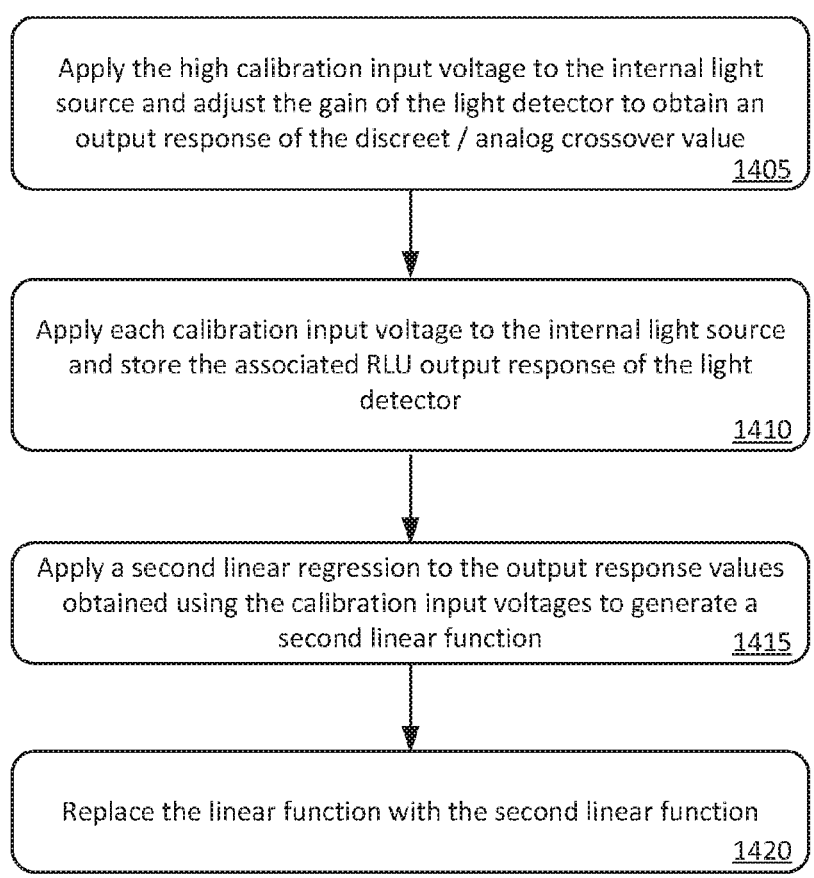
FIG. 14 is a flowchart depicting an example re-linearization method for a luminometer, according to an embodiment.

FIG. 14 illustrates a flowchart depicting a calibration method 1400. The method 1400 can be performed by, for example luminometer electrical system 900 of FIG. 9A. At step 1405, the test cycle calibration module 940 can apply the high calibration input voltage to the internal light source (i.e., LED 620) and adjust the gain of the light detector (i.e., PMT 630) to obtain an RLU output response that equals the discreet/analog crossover 1015. The RLU output response is obtained using the digitized assay photon count 970. At step 1410 the test cycle calibration module 940 can apply each calibration input voltage to the internal light source and store the associated RLU output response of the light detector 630. The associated RLU output response for the calibration in the calibration zone $Z_C$ may be the digitized assay photon count 970. The calibration input voltages were each determined during the master calibration as described in method 1200. At step 1415, the test cycle calibration module 940 can apply a second linear regression to the most recent RLU output response values obtained using the calibration input voltages. The linear regression will provide an updated slope (m) and offset (b) for the linear function. At step 1420, the test cycle calibration module 940 can replace the old linear function with the new linear function in the luminometer computer system memory.

FIG. 15 illustrates a block diagram of an example computer system 1500 usable for performing signal linearity extension as described in detail herein. The computing device 1500 can be or include, for example, a laptop computer, desktop computer, tablet, e-reader, smart phone or mobile device, smart watch, personal data assistant (PDA), or other electronic device.

The computing device 1500 can include a processor 1640 interfaced with other hardware via a bus 1505. A memory 1510, which can include any suitable tangible (and non-transitory) computer readable medium, such as RAM, ROM, EEPROM, or the like, can embody program components (e.g, instructions 1515) that configure operation of the computing device 1700. In some examples, the computing device 1500 can include input/output ("I/O") interface components 1525 (e.g., for interfacing with a display 1545, keyboard, or mouse) and additional storage 1530.

The computing device 1500 can include network components 1520. Network components 1520 can represent one or more of any components that facilitate a network connection. In some examples, the network components 1520 can facilitate a wireless connection and include wireless interfaces such as IEEE 802.11, Bluetooth, or radio interfaces for accessing cellular telephone networks (e.g., a transceiver/antenna for accessing CDMA. GSM, UMTS, or other mobile communications network). In other examples, the network components 1520 can be wired and can include interfaces such as Ethernet, USB, or IEEE 1394.

Although FIG. 15 depicts a single computing device 1500 with a single processor 1540, the system can include any number of computing devices 1500 and any number of processors 1540. For example, multiple computing devices 1500 or multiple processors 1540 can be distributed over a wired or wireless network (e.g., a Wide Area Network, Local Area Network, or the Internet). The multiple computing devices 1500 or multiple processors 1540 can perform any of the steps of the present disclosure individually or in coordination with one another.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations Embodiments of the present disclosure have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure.

It is to be understood that the figures and descriptions of embodiments of the present disclosure have been simplified to illustrate elements that are relevant for a clear understanding of the present disclosure. Those of ordinary skill in the art will recognize, however, that these and other elements may be desirable. However, because such elements are well known in the art, and because they do not facilitate a better understanding of the present disclosure, a discussion of such elements is not provided herein. It should be appreciated that the figures are presented for illustrative purposes and not as construction drawings. Omitted details and modifications or alternative embodiments are within the purview of persons of ordinary skill in the art.

The examples presented herein are intended to illustrate potential and specific implementations of the present disclosure. It can be appreciated that the examples are intended primarily for purposes of illustration of the present disclosure for those skilled in the art. There may be variations to these diagrams or the operations described herein without departing from the spirit of the present disclosure.

Furthermore, whereas particular embodiments of the present disclosure have been described herein for the purpose of illustrating the present disclosure and not for the purpose of limiting the same, it will be appreciated by those of ordinary skill in the art that numerous variations of the details, materials and arrangement of elements, steps, structures, and/or parts may be made within the principle and scope of the present disclosure without departing from the present disclosure as described in the claims.

All patents, patent publications, patent applications, journal articles, books, technical references, and the like discussed in the instant disclosure are incorporated herein by reference in their entirety for all purposes.

What is claimed is:

1. A system for performing an assay, the system comprising:
 a chassis, comprising:
  a reaction vessel chamber comprising
   a first portion of a kinematic spherical joint adjacent to a bottom of the reaction vessel chamber, and
   a first portion of a kinematic cylindrical joint adjacent to a top of the reaction vessel chamber, and
  a light passage comprising a first end and a second end, the light passage intersecting the reaction vessel chamber;

a cap that, when in a closed configuration, forms a dark chamber by preventing light emitted by external light sources from entering the reaction vessel chamber and from entering the light passage, and, when in an open configuration, provides access to the reaction vessel chamber;

a calibration light source optically coupled to the first end of the light passage; and a light detector optically coupled to the second end of the light passage, the light detector comprising
   a sensing element for receiving light from the light passage, and
   an aperture for receiving light from the light passage and that provides a shielded view of light from the light passage to the sensing element.

2. The system of claim 1, wherein the aperture provides a shielded view of a reaction vessel positioned within the reaction vessel chamber.

3. The system of claim 2, wherein the reaction vessel comprises a sample that comprises a meniscus at a top of the sample, wherein the shielded view excludes the meniscus.

4. The system of claim 1, wherein the light detector further comprises a light detector bracket comprising the aperture.

5. The system of claim 4, wherein the light detector bracket couples the light detector to the chassis.

6. The system of claim 1, wherein the aperture has a diameter of 8.5 cm or less.

7. The system of claim 1, wherein the dark chamber is formed when an opening angle between the cap and the chassis is seven degrees or less from the closed configuration.

8. The system of claim 1, further comprising:
a cap arm coupled to the cap; and
a motor coupled to the cap arm, wherein operation of the motor changes a configuration of the cap between the closed configuration and the open configuration.

9. The system of claim 1, further comprising:
a cap sensor that senses the configuration of the cap; and
a shutter communicatively coupled to the cap sensor and configured to block light present in the light passage from reaching the sensing element when the shutter is closed, wherein the shutter closes when the cap sensor indicates the cap is in the open configuration.

10. The system of claim 1, further comprising:
a heating element attached to an external portion of the chassis;
a thermistor positioned within a thermistor passage of the chassis and electrically coupled to a control system; and
a thermal barrier positioned below the chassis;
wherein:
   the chassis is aluminum, and
   the heating element is activated by the control system based on a temperature of the chassis as measured by the thermistor to maintain a predetermined temperature of the chassis.

11. The system of claim 10, wherein the chassis further comprises a housing, the housing enclosing the reaction vessel chamber, the light passage, the thermistor passage, and the thermistor.

12. The system of claim 1, further comprising:
a thermal cavity within the chassis, the light detector at least partially positioned within the thermal cavity;
a thermal cover positioned over an opening of the thermal cavity; and
a thermally conductive gasket that thermally couples the thermal cover to the chassis;
wherein the thermal cavity and the thermal cover define an enclosed volume; and
wherein the light detector is positioned within the enclosed volume.

13. The system of claim 1, further comprising:
a reaction vessel comprising:
   a fin that, when the reaction vessel is placed in the reaction vessel chamber, forms a second portion of the kinematic cylindrical joint, and
   a nose that, when the reaction vessel is placed in the reaction vessel chamber, forms a second portion of the kinematic spherical joint;
wherein the reaction vessel is positioned within the reaction vessel chamber by the kinematic cylindrical joint and the kinematic spherical joint.

14. The system of claim 13, wherein:
an opening to the reaction vessel chamber includes a tapered portion adapted to guide the reaction vessel into the reaction vessel chamber;
the tapered portion is adjacent the first portion of the kinematic cylindrical joint;
the fin is spaced less than a fin thickness from the tapered portion when the reaction vessel is positioned within the reaction vessel chamber by the kinematic cylindrical joint and the kinematic spherical joint; and
the tapered portion is configured to provide a relief clearance for the fin upon removal of the reaction vessel from the reaction vessel chamber.

15. The system of claim 1, wherein the calibration light source comprises:
an aluminum housing having an aperture positioned at the first end of the light passage;
a light emitting diode ("LED"); and
a photodiode; and
the system further comprising a filter positioned between the first end of the light passage and the aperture.

16. The system of claim 1, wherein the light detector comprises:
a photomultiplier tube configured to measure a relative light unit ("RLU") of light within the light passage.

17. The system of claim 1, wherein the reaction vessel chamber is for holding a reaction vessel, the reaction vessel chamber comprising:
a first reaction vessel locating feature adapted to interface with a first feature of the reaction vessel and thereby translationally couple the reaction vessel chamber to the reaction vessel at a first point in three mutually orthogonal directions;
a second reaction vessel locating feature adapted to interface with a second feature of the reaction vessel and thereby translationally couple the reaction vessel chamber to the reaction vessel at a second point, spaced from the first point, in two mutually orthogonal directions, the two mutually orthogonal directions each orthogonal to a chamber axis defined by the reaction vessel chamber and located on the first point and the second point;
wherein the reaction vessel is substantially axisymmetric about a central axis;
wherein the chamber axis on the first point and the second point is coincident with the central axis of the reaction vessel; and
wherein the reaction vessel is located within the reaction vessel chamber except for rotation about the chamber axis.

18. A system for performing an assay, the system comprising:
- a chassis, comprising:
  - a reaction vessel chamber, and
  - a light passage comprising a first end and a second end, the light passage intersecting the reaction vessel chamber;
- a cap that, when in a closed configuration, forms a dark chamber by preventing light emitted by external light sources from entering the reaction vessel chamber and from entering the light passage, and, when in an open configuration, provides access to the reaction vessel chamber;
- a calibration light source optically coupled to the first end of the light passage; and
- a light detector optically coupled to the second end of the light passage, the light detector comprising
  - a sensing element for receiving light from the light passage,
  - an aperture for receiving light from the light passage and having a diameter of 8.5 cm or less.

19. A system for performing an assay, the system comprising:
- a chassis, comprising:
  - a reaction vessel chamber, and
  - a light passage comprising a first end and a second end, the light passage intersecting the reaction vessel chamber;
- a cap that, when in a closed configuration, forms a dark chamber by preventing light emitted by external light sources from entering the reaction vessel chamber and from entering the light passage, and, when in an open configuration, provides access to the reaction vessel chamber;
- a calibration light source optically coupled to the first end of the light passage;
- a light detector optically coupled to the second end of the light passage, the light detector comprising
  - a sensing element for receiving light from the light passage,
  - an aperture for receiving light from the light passage;
- a cap sensor that senses the configuration of the cap; and
- a shutter communicatively coupled to the cap sensor and configured to block light present in the light passage from reaching the sensing element when the shutter is closed, wherein the shutter closes when the cap sensor indicates the cap is in the open configuration.

20. A system for performing an assay, the system comprising:
- a chassis, comprising:
  - a reaction vessel chamber, and
  - a light passage comprising a first end and a second end, the light passage intersecting the reaction vessel chamber;
- a cap that, when in a closed configuration, forms a dark chamber by preventing light emitted by external light sources from entering the reaction vessel chamber and from entering the light passage, and, when in an open configuration, provides access to the reaction vessel chamber;
- a calibration light source optically coupled to the first end of the light passage;
- a light detector optically coupled to the second end of the light passage, the light detector comprising
  - a sensing element for receiving light from the light passage, and
  - an aperture for receiving light from the light passage and that provides a shielded view of light from the light passage to the sensing element;
- a heating element attached to an external portion of the chassis;
- a thermistor positioned within a thermistor passage of the chassis and electrically coupled to a control system; and
- a thermal barrier positioned below the chassis;
- wherein:
  - the chassis is aluminum, and
  - the heating element is activated by the control system based on a temperature of the chassis as measured by the thermistor to maintain a predetermined temperature of the chassis.

* * * * *